(12) United States Patent
Ravenelle et al.

(10) Patent No.: US 11,098,009 B2
(45) Date of Patent: Aug. 24, 2021

(54) AMIDINE SUBSTITUTED ANALOGUES AND USES THEREOF

(71) Applicant: Verlyx Pharma Inc., Pointe-Claire (CA)

(72) Inventors: François Ravenelle, Pointe-Claire (CA); Michel Therien, Pointe-Claire (CA); Helmi Zaghdane, Pointe-Claire (CA)

(73) Assignee: Verlyx Pharma Inc., Pointe-Claire (CA)

( * ) Notice: Subject to any disclaimer, the term of this patent is extended or adjusted under 35 U.S.C. 154(b) by 0 days.

(21) Appl. No.: 16/470,922

(22) PCT Filed: Dec. 21, 2017

(86) PCT No.: PCT/CA2017/051576
§ 371 (c)(1),
(2) Date: Jun. 18, 2019

(87) PCT Pub. No.: WO2018/112649
PCT Pub. Date: Jun. 28, 2018

(65) Prior Publication Data
US 2020/0087252 A1    Mar. 19, 2020

Related U.S. Application Data

(60) Provisional application No. 62/438,128, filed on Dec. 22, 2016.

(51) Int. Cl.
*A61P 37/00* (2006.01)
*A61P 37/06* (2006.01)
*C07C 257/18* (2006.01)

(52) U.S. Cl.
CPC .................. *C07C 257/18* (2013.01)

(58) Field of Classification Search
CPC ......... A61P 37/00; A61P 37/06; C07C 257/18
See application file for complete search history.

(56) References Cited

U.S. PATENT DOCUMENTS

| | | |
|---|---|---|
| 5,998,482 A | 12/1999 | David et al. |
| 2006/0122279 A1 | 6/2006 | Burns et al. |
| 2007/0093424 A1 | 4/2007 | Burns et al. |
| 2007/0197658 A1 | 8/2007 | David et al. |
| 2007/0232674 A1 | 10/2007 | Burns et al. |
| 2010/0323993 A1 | 12/2010 | Berglund et al. |

FOREIGN PATENT DOCUMENTS

| | | |
|---|---|---|
| CA | 2391085 | 5/2001 |
| DE | 2833135 | 2/1980 |
| GB | 1288376 | 9/1972 |
| JP | H08333324 | 12/1996 |
| JP | H0975446 | 3/1997 |
| WO | 0197794 | 12/2001 |

OTHER PUBLICATIONS

RN 39141-26-9, 1984, registry compound.*
Schill et al., 1981, caplus an 1981:509090.*
CAS #39141-26-9.
CAS #39141-30-5.
CAS #60890-58-6.
David et al. (1994) "Interaction of cationic amphiphilic drugs with lipid A: Implications for development of endotoxin antagonists" *Biochimica et Biophysica Acta* 1212: 167-175.
Fenton et al. (1998) "LPS-binding proteins and receptors" *Journal of Leukocyte Biology*: 25-32.
Geratz et al. (1978) "Specific inhibition of platelet agglutination and aggregation by aromatic amidino compounds" *Thrombos. Haemostas.*: 411-425.
International Search Report and Written Opinion for PCT/CA2017/051576 dated Apr. 18, 2018.
Mischiati et al. (2001) "Aromatic Polyamidines Inhibiting the Tat-Induced HIV-1 Transcription Recognize Structured TAR-RNA" *Antisense & Nucleic Acid Drug Development*: 209-217.
Rosenthal et al. (1992) "Pentamidine blocks the pathophysiologic effects of endotoxemia through inhibition of Cytokine Release" *Toxicology and Applied Pharmacology*: 222-228.
Schill et al. (1981) "Inhibitors of acrosomal proteinase as antifertility agents. A problem of acrosomal membrane permeability" *International Journal of Andrology*: 25-38.
Shrestha (2004) "Design, Syntheses, and Evaluation of Lipopolyamines as Anti-Endoxin Agents" (*Thesis*): 23-26.
Sil et al. (2013) "Biophysical mechanisms of the neutrolization of endotoxins by Lipopolyamines" *The Open Biochemistry Journal* 7: 82-93.
Stokes et al. (2017) "Pentamidine sensitizes Gram-negative pathogens to antibiotics and overcomes acquired colistin resistance" *PubMed Central Canada*: 1-21.
Extended European Search Report for PCT/CA2017/051576 dated Jul. 22, 2020.
Nastruzzi et al. (1989) "Inhibition of 'in vitro' tumor cell growth by aromatic polyamidines exhibiting antiproteinase activity" Clin. Expl. Metastasis, 7(1): 25-39.

(Continued)

*Primary Examiner* — Sun Jae Yoo
(74) *Attorney, Agent, or Firm* — Edward J. Baba; Bozicevic, Field & Francis LLP

(57) ABSTRACT

The present application relates to amidine substituted analogues as shown in formula I and uses thereof as an anti-inflammatory agent and/or for the treatment of an immunological disorder or of an inflammatory bowel disease including ulcerative colitis, Crohn's diseases, collagenous colitis and lymphocytic colitis.

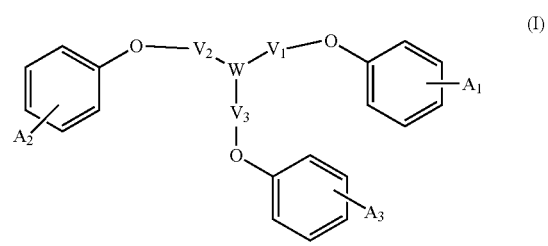

(I)

14 Claims, 3 Drawing Sheets

(56) References Cited

OTHER PUBLICATIONS

Parrish. et al.( 1978) "Structure-activity relationships for the inhibition of acrosin by benzamidine derivatives" Journal of Medicinal Chemistry, 21(11): 1132-1136.
Tidwell et al. (1976) "Aromatic Tris-Amidines: A New Class of Highly Active Inhibitors of Trypsin-Like Proteases" Biochimica et Biophysica Acta, 445: 729-738.

* cited by examiner

Fig 1. ALT Activity, 6 hours post liver injury (study a)
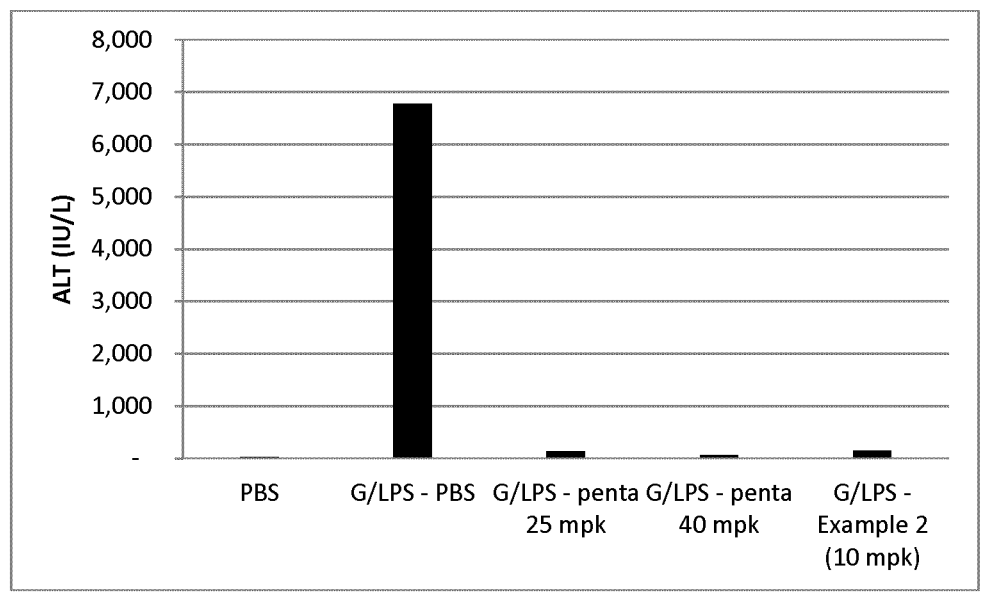
Fig.2
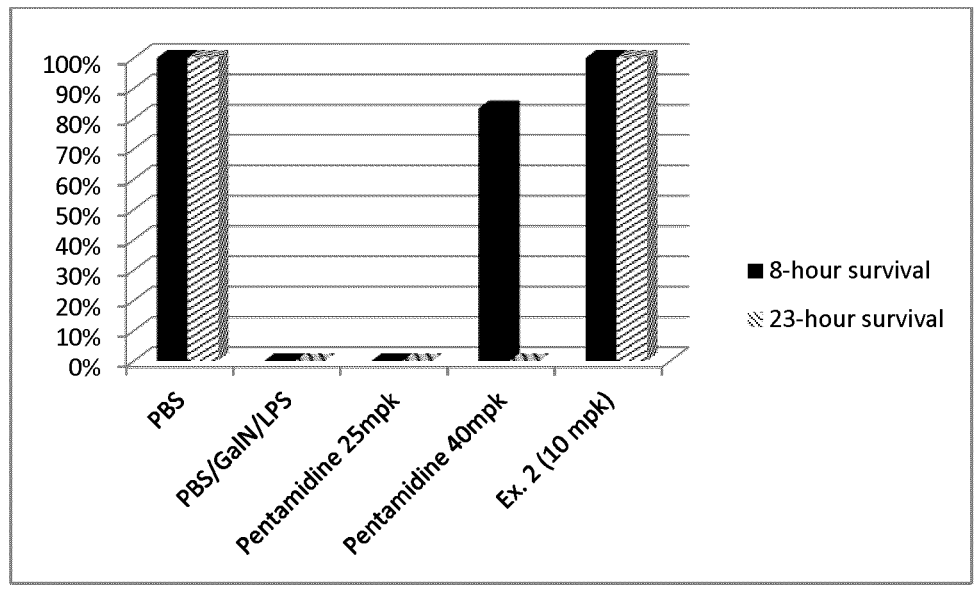

Fig. 3. ALT Activity, 6 hours post liver injury (Study b)
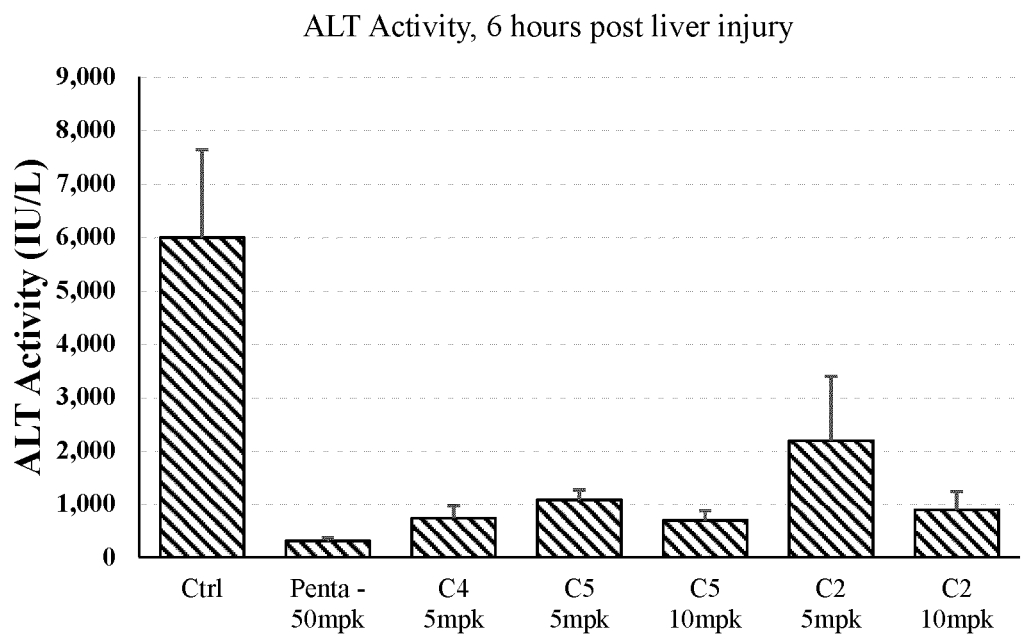
Fig. 4. ALT Activity, 6 hours post liver injury (Study c)
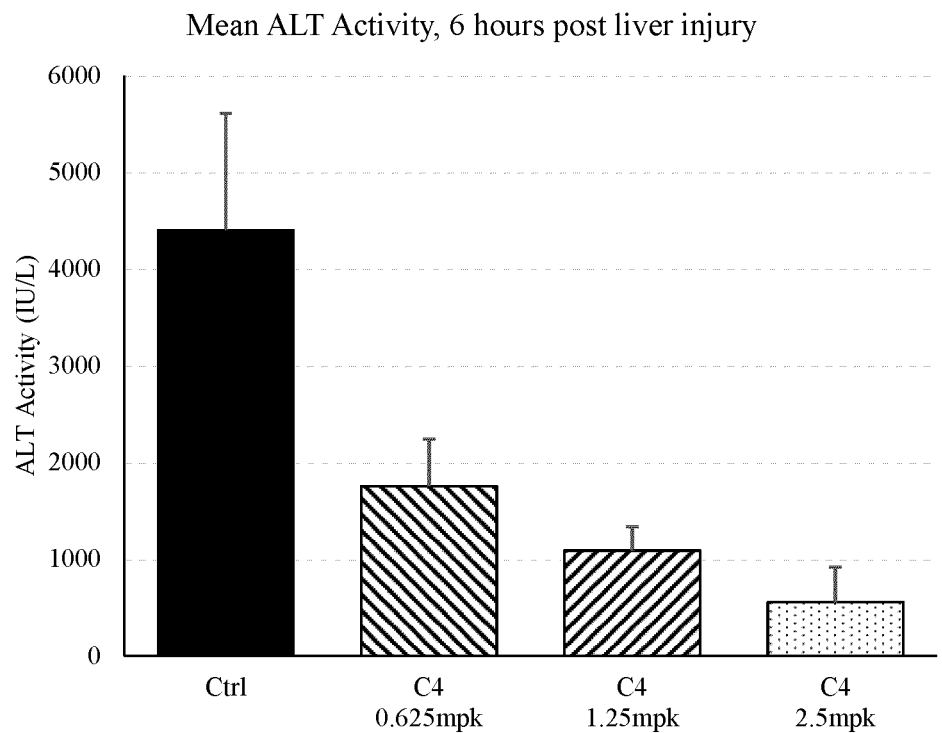

AMIDINE SUBSTITUTED ANALOGUES AND USES THEREOF

This application claims priority from U.S. application 62/438,128 filed Dec. 22, 2016 which is herein incorporated by reference.

This application relates to novels compounds, pharmaceutical compositions comprising same and uses thereof.

According to one aspect, there is provided a compound of formula (I):

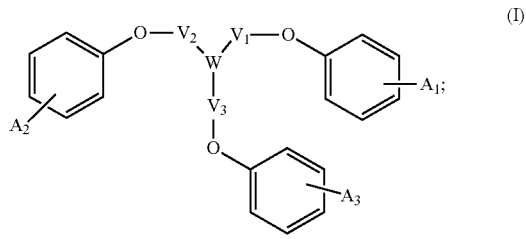

(I)

or a pharmaceutically acceptable salt thereof, wherein:

W is $C_1$-$C_{16}$ alkyl or $C_6$-$C_{10}$ aryl, each optionally substituted by 1 to 3 substituents;

$V_1$, $V_2$ and $V_3$ are each independently -$J_1$- or —$OJ_1$-, wherein $J_1$ is an optionally substituted by 1 to 3 substituents $C_1$-$C_{16}$ alkyl optionally interrupted by —O—; and $A_1$, $A_2$ and $A_3$ are each independently —C(=NH)—$NH_2$ or —C(=NH)—NHOH.

In one aspect, when $V_1$, $V_2$ and $V_3$ are —$(CH_2)_{1-6}$—; then at least one of $A_1$, $A_2$ and $A_3$ is C(=NH)—NHOH.

According to one aspect, there is provided a pharmaceutical composition comprising a compound as defined herein with a pharmaceutically acceptable carrier, diluent and excipient.

According to another aspect, there is provided the use of a compound or composition as defined herein as an anti-inflammatory agent.

According to another aspect, there is provided the use of a compound or composition as defined herein for the treatment of an immunological disorder or of an inflammatory bowel disease including ulcerative colitis, Crohn's diseases, collagenous colitis and lymphocytic colitis.

According to another aspect, there is provided the use of a compound or composition as defined herein in the manufacture of a medicament for the treatment of an immunological disorder or of an inflammatory bowel disease including ulcerative colitis, Crohn's diseases, collagenous colitis and lymphocytic colitis.

According to another aspect, there is provided a method for treating an immunological disorder, or an inflammatory bowel disease including ulcerative colitis, Crohn's diseases, collagenous colitis and lymphocytic colitis in a subject in need thereof which comprises administering a therapeutically effective amount of a compound as defined herein.

Combinations of substituents and variables envisioned by the present description are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

In a further aspect, the compound of formula (I) is represented by:

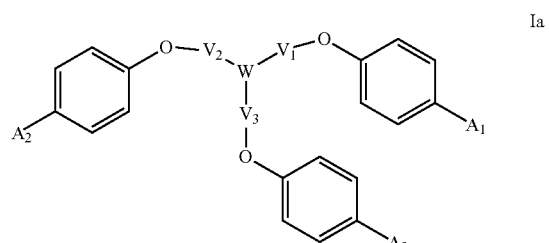

Ia

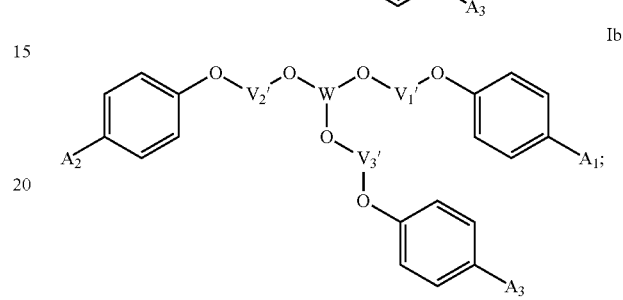

Ib

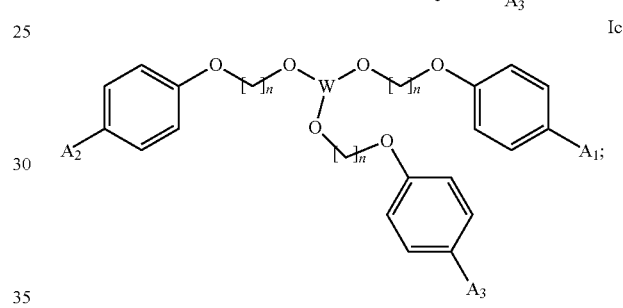

Ic

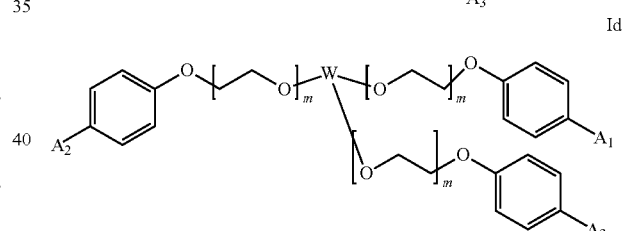

Id

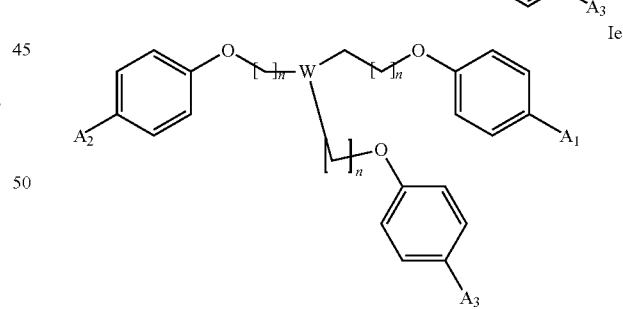

Ie wherein W, $A_1$, $A_2$ and $A_3$ are as defined herein; $V_{1'}$, $V_{2'}$, and $V_{3'}$ are each independently -$J_1$- as defined herein; each n is independently an integer chosen between 1 and 12 and each m is independently an integer chosen between 1 and 6.

In one aspect, the following embodiments are present alone or in combination if applicable:

In one aspect, $V_1$, $V_2$, $V_3$, $V_{1'}$, $V_{2'}$ and $V_{3'}$ are independently $C_3$-$C_{12}$ alkyl optionally substituted by 1 to 3 substituents and wherein the units are optionally interrupted by —O—.

In one aspect, $V_1$, $V_2$, $V_3$, $V_{1'}$, $V_{2'}$ and $V_{3'}$ are independently $C_5$-$C_{12}$ alkyl optionally substituted by 1 to 3 substituents.

In one aspect, $V_1$, $V_2$, $V_3$, $V_{1'}$, $V_{2'}$ and $V_{3'}$ are independently a polydisperse or monodisperse polymer comprising repeating units as defined herein.

In one aspect, the average molecular weight (Mn) of $V_1$, $V_2$, $V_3$, $V_{1'}$, $V_{2'}$ and $V_{3'}$ are independently between 200 and 5000; between 400 and 2000; between 600 and 1500; between 800 and 1200 or between 900 and 1100. The Mn represents the number average molecular weight of the polymer and is defined by the following formula:

$$Mn = \frac{\sum N_i M_i}{\sum N_i};$$

wherein $M_i$ is the molecular weight of a chain and $N_i$ is the number of chain of that molecular weight.

For example, in

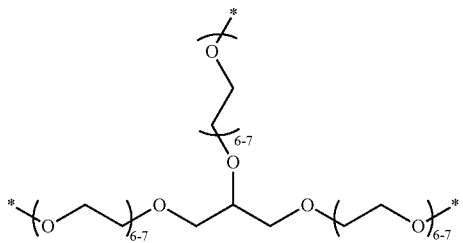

wherein each* represent the attachment point to the phenyl group, then the Mn of the core is about 1000.

In a further aspect n and m represent the average number of repeating units of the polymer chains, and therefore each arm of the compound may the same or may be of different length.

In one aspect, each n is independently an integer chosen between 4 and 12.

In one aspect, each n is independently an integer chosen between 4 and 8, 4 and 6. In a further aspect, n is 6 or n is 8.

In one aspect, each m is independently an integer chosen between 2 and 6.

In a further aspect m is 2, 3, 4, 5 or 6.

In one aspect, each $J_1$ is independently $C_3$-$C_{12}$ alkyl or —$OC_3$-$C_{12}$ alkyl optionally interrupted by —O—.

In one aspect, $J_1$ is independently $C_5$-$C_{12}$ alkyl or —$OC_5$-$C_{12}$ alkyl optionally interrupted by —O—.

In one aspect, $J_1$ is independently $C_3$-$C_{12}$ alkyl or —$OC_3$-$C_{12}$ alkyl.

In one aspect, $J_1$ is independently $C_5$-$C_{12}$ alkyl or —$OC_5$-$C_{12}$ alkyl.

In one aspect, W is phenyl.

In a further aspect W is optionally substituted phenyl.

In a further aspect wherein W is phenyl.

In a further aspect wherein W is $C_1$-$C_3$ alkyl.

In a further aspect wherein W is a carbon atom.

In one aspect, the 1 to 3 substituents of the alkyl, are independently chosen from halogens, oxo, —$NR_dR_e$, —$CONR_dR_e$, =NO—$R_e$, —$NR_dCOR_e$, carboxy, —C(=$NR_d$)$NR_eR_f$, azido, cyano, $C_{1-6}$ alkyloxy, $C_{2-6}$ alkenyloxy, $C_{2-6}$ alkynyloxy, —N($R_d$)C(=$NR_e$)—$NR_fR_g$, hydroxyl, nitro, nitroso, —N($R_h$)$CONR_iR_j$, —S(O)$_{0-2}R_a$, —C(O)$R_a$, —C(O)$OR_a$, —$SO_2NR_aR_b$, —$NR_aSO_2R_b$, —$NR_aSO_2NR_bR_c$, —$CR_aN$=$OR_b$, and/or —$NR_aCOOR_b$, wherein $R_a$-$R_j$ are each independently H, $C_{1-4}$ alkyl, $C_{2-4}$ alkenyl, or $C_{2-4}$ alkynyl; and the 1 to 3 substituents of the aryl are independently chosen from halogens, $NR_dR_e$, —$CONR_dR_e$, —$NR_dCOR_e$, carboxy, —C(=$NR_d$)$NR_eR_f$, azido, cyano, —N($R_d$)C(=$NR_e$)$NR_fR_g$, hydroxyl, nitro, nitroso, —N($R_h$)$CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, —S(O)$_{0-2}R_a$, optionally substituted 5-12 member heteroaryl, optionally substituted 6-18 member heteroaralkyl, optionally substituted 3-12 member heterocycle, optionally substituted 4-18 member heterocycle-alkyl, —C(O)$R_a$, —C(O)$OR_a$, —$SO_2NR_aR_b$, —$NR_aSO_2R_b$, —$NR_aSO_2NR_bR_c$, —$CR_aN$=$OR_b$, $OCONR_eR_f$, —C(=S)$NR_dR_e$ and/or —$NR_aCOOR_b$, wherein $R_a$-$R_j$ are each independently H, $C_{1-4}$ alkyl, $C_{2-4}$ alkenyl, or $C_{2-4}$ alkynyl.

In another embodiment the compounds of formula (I) are selected from the examples as shown in Table 1.

TABLE 1

| Example | Name | Structure |
|---|---|---|
| 1 | Trihexamidine formate | 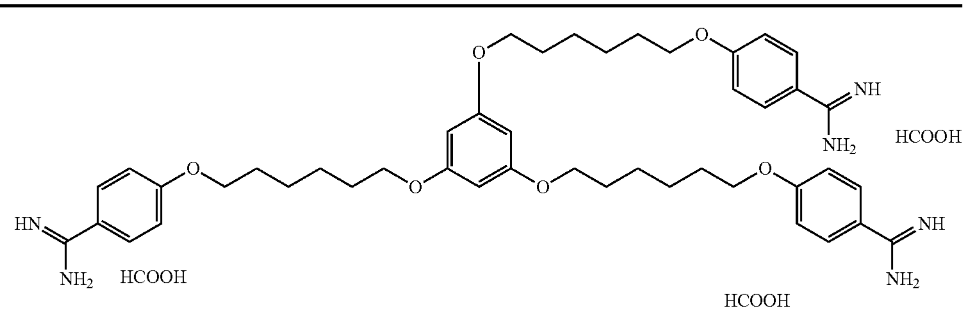 |

TABLE 1-continued

| Example | Name | Structure |
|---|---|---|
| 2 | Trihexamidine isethionate | 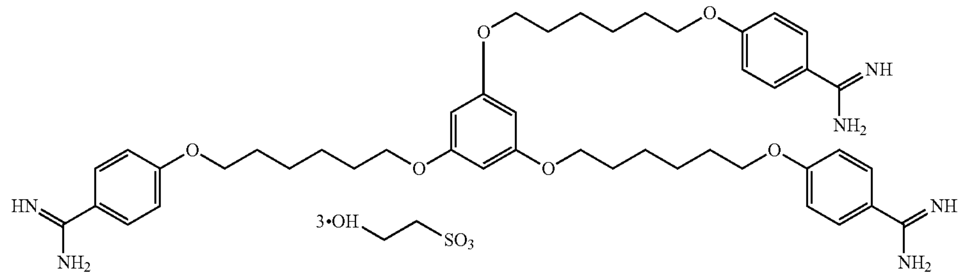 |
| 3 | Trioctamidine isethionate | 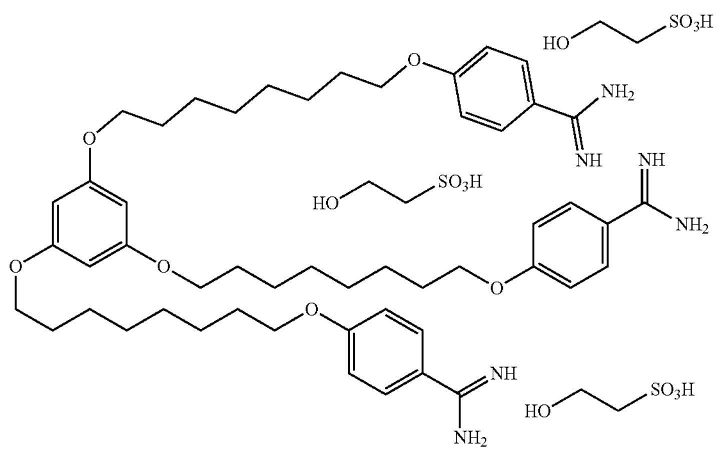 |
| 4 | Tripropamidine formate | 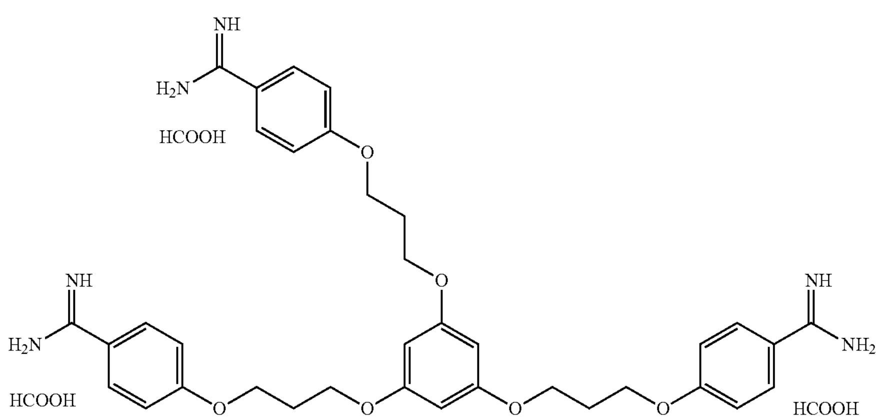 [SMILES: "HCOOH" ; N=C(N)c1ccc(OCCCOc2cc(OCCCOc3ccc(C(=N)N)cc3)cc(OCCCOc3ccc(C(=N)N)cc3)c2)cc1 ; "HCOOH" ; "HCOOH"] |
| 5 | Triamidine formate (chain average Mn 1000) | 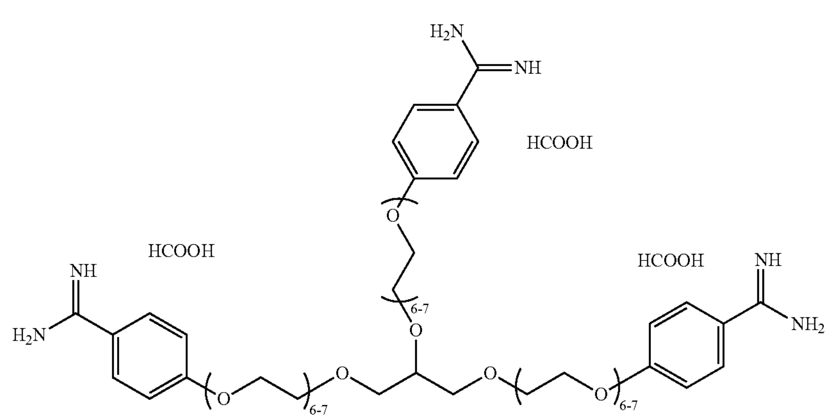 |

Methods, Uses, Formulation and Administration

Treatment of Immunological Disorders

In one aspect, the compounds of the present description may be used for treating immunological disorders.

In one aspect the immunological disorder is Rheumatoid arthritis, lupus, multiple sclerosis, type-1 diabetes, psoriasis, Grave's disease, Hashimoto's thyroiditis, vasculitis or myasthenia gravis.

Anti-Inflammatory Agent

In one aspect, the compounds of the present description may be used as anti-inflammatory agent.

Treatment of Inflammatory Bowel Disease (IBD)

In one aspect, the compounds of the present description may be used to treat Inflammatory Bowel Disease (IBD).

In one aspect, the compounds of the present description may be used to treat Crohn's disease (CD) or ulcerative colitis (UC).

Treatment of Cancer

In one aspect, the compounds of the present description may be used for treating cancer.

In one aspect the cancer is squamous cell carcinoma, larger cell carcinoma of the lymph node, breast cancer, colon cancer, liver cancer, lung carcinoma, melanoma, pancreatic cancer, leukemia, non-small cell lung cancer, colon cancer, central nervous system (CNS) cancer, ovarian cancer, renal cancer or prostate cancer In one aspect the cancer is liver cancer.

In one aspect, the liver cancer is intrahepatic bile duct cancer or hepatocarcinoma.

In one embodiment there is provided, the uses or methods as defined herein, for treating liver dominant colorectal cancer metastasis.

Liver dominant cancer metastasis refers to metastases that are mainly located in the liver (e.g., determination of size, number and type of lesions).

Liver limited cancer metastasis refers to metastases that are only located in the liver (e.g., determination of size, number and type of lesions).

In one aspect, the cancer condition or status of the patient is determined in accordance with the Response Evaluation Criteria in Solid Tumours (RECIST). See for example EUROPEAN JOURNAL OF CANCER 45 (2009) 228-247

In one embodiment there is provided, the uses or methods as defined herein, for treating metastasized cancer.

In one aspect, the patient has one or more of the following conditions:

Inoperable liver tumors, minor lung or bone metastasis or abnormal hepatic enzyme level.

In one aspect, the cancer patient is treated as long as the disease is stable or until there is tumor progression (e.g., diseases progression, appearance of new lesions etc.).

In one embodiment there is provided, the use or method of as defined herein wherein the primary cancer originates from pancreatic cancer cells, colon cancer cells, breast cancer cells or ovarian cancer cells.

In one embodiment the compounds are used in combination with standard chemotherapy.

In one embodiment there is provided, a pharmaceutical composition comprising at least one compound as defined herein or a pharmaceutically acceptable salt thereof and one or more further therapeutic agent indicated for the treatment of cancer.

In one embodiment there is provided, a pharmaceutical composition comprising one compound as defined or a pharmaceutically acceptable salt thereof and one or more further therapeutic agent for inhibiting the proliferation of cancer cells or for the treatment of cancer.

Other Liver Conditions or Diseases

In one aspect, the compounds of the present description may also be used for the treatment of liver conditions. Liver conditions include Liver cancer; Primary biliary cirrhosis; Autoimmune Hepatitis; Chronic liver disease; Cirrhosis of the liver; Hepatitis; Viral Hepatitis; Hepatitis A; Hepatitis B; Chronic Hepatitis B; Hepatitis C; Chronic Hepatitis C; Hepatitis D; Hepatitis E; Hepatitis X; Liver failure; Jaundice; Neonatal Jaundice; Hepatoma; Liver cancer; Liver abscess; Alcoholic liver disease; Hemochromatosis; Wilson's Disease; Portal hypertension; Primary sclerosing cholangitis; Sarcoidosis; Tapeworms; Alveolar Hydatid Disease; Fascioliasis; Schistosomiasis; Gaucher Disease; Zellweger Syndrome; Alcoholism; Hepatitis Virus—Teratogenic Agent; Human carcinogen—Chronic Hepatitis B viral infection; Human carcinogen—Chronic Hepatitis C viral infection; Probable human carcinogen—*Clonorchis sinensis* Infection; Drug-induced liver damage—Clindamycin; Drug-induced liver damage—Quinolone; Drug-induced liver damage—Spectinomycin; Drug-induced liver damage—Sulfones; Drug-induced liver damage—5-Fluorocytosine; Drug-induced liver damage—Allopurinol; Drug-induced liver damage—Amphotericin; Drug-induced liver damage—Anabolic C-17; Drug-induced liver damage—Anesthetic agent; Drug-induced liver damage—Antianginal agents; Drug-induced liver damage—Antiarrhythmics; Drug-induced liver damage—Antibiotics; Drug-induced liver damage—Anticoagulants; Drug-induced liver damage—anticonvulsives; Drug-induced liver damage—Antifungals; Drug-induced liver damage—Antihyperlipidemic agents; Drug-induced liver damage—Antihypertensives; Drug-induced liver damage—Antineoplastic agents; Drug-induced liver damage—Antithyroid drugs; Drug-induced liver damage—antituberculous agents; Drug-induced liver damage—antiviral medication; Drug-induced liver damage—Benzodiazepine; Drug-induced liver damage—British anti-Lewisite penicillamine; Drug-induced liver damage—Butyrophenone; Drug-induced liver damage—Cephalosporin; Drug-induced liver damage—Chloramphenicol; Drug-induced liver damage—Chloroform; Drug-induced liver damage—Cimetidine; Drug-induced liver damage—Colchicine; Drug-induced liver damage—Cyclopropane; Drug-induced liver damage—Cycloserine; Drug-induced liver damage—Cytarabine; Drug-induced liver damage—Dantrolene; Drug-induced liver damage—Diflunisal; Drug-induced liver damage—Disulfiram; Drug-induced liver damage—Diuretic Agents; Drug-induced liver damage—endocrine agent; Drug-induced liver damage—Erythromycin estolate; Drug-induced liver damage—Erythromycin ethyl succinate; Drug-induced liver damage—Ethionamide; Drug-induced liver damage—Fenoprofen; Drug-induced liver damage—Glucocorticoids; Drug-induced liver damage—Griseofulvin; Drug-induced liver damage—Halothane; Drug-induced liver damage—Ibuprofen; Drug-induced liver damage—idoxuridine; Drug-induced liver damage—Indomethacin; Drug-induced liver damage—Iodide ion; Drug-induced liver damage—Isoniazid; Drug-induced liver damage—Ketoconazole; Drug-induced liver damage—Mephenytoin; Drug-induced liver damage—Methoxyflurane; Drug-induced liver damage—monoamine oxidase inhibitors; Drug-induced liver damage—Naproxen; Drug-induced liver damage—Nitrofuran; Drug-induced liver damage—Nitrous Oxide; Drug-induced liver damage—Novobiocin; Drug-induced liver damage—Oral hypoglycemics; Drug-induced liver damage—p-aminosalicylic acid; Drug-induced liver damage—Penicillin; Drug-induced liver damage—Phenobarbital; Drug-induced liver damage—Phenothiazines; Drug-induced liver damage—Phenylbutazone; Drug-induced liver damage—Phenytoin; Drug-induced liver damage—psychotropic agents; Drug-induced liver damage—Ranitidine; Drug-induced liver damage—Rifampicin; Drug-induced liver damage—Salicylate; Drug-induced liver damage—Saramycetin; Drug-induced liver damage—Steroids; Drug-induced liver damage—Sulfonamide; Drug-induced liver damage—Sulindac; Drug-induced liver damage—Tamoxifen; Drug-induced liver damage—Telithromycin; Drug-induced liver damage—Tetracycline; Drug-induced liver damage—Thioxanthene; Drug-induced liver damage—Thorotrast; Drug-induced liver damage—tricyclic antidepressant; Drug-induced liver damage—Valproic Acid; Drug-induced liver damage—Vidarabine; Drug-induced liver damage—Vitamin A; Drug-induced liver damage—xenylamine; Drug-induced liver damage—Zoxazolamine; Drugs-induced liver damage—Ether; Occupational liver damage—1,1,1-Tetrachloroethane; Occupational liver damage—1,1,2-Tetrachloroethane; Occupational liver damage—1,2-Dibromoethane; Occupational liver damage—1,2-Dichloroethane; Occupational liver damage—2-acetylamino-fluorene; Occupational liver damage—2-Nitropropane; Occupational liver damage—3,3-Dichlorobenzidine; Occupational liver damage—4-Dimethylaminoazobenzene; Occupational liver damage—Acetates; Occupational liver damage—Acetonitrile; Occupational liver damage—Acrylonitrile; Occupational liver damage—Alcohol; Occupational liver damage—Alicyclic Hydrocarbons; Occupational liver damage—Aliphatic Amines; Occupational liver damage—Aliphatic Hydrocarbons; Occupational liver damage—Aliphatic hydrogenated hydrocarbons; Occupational liver damage—Allyl alcohol; Occupational liver damage—Amyl acetate; Occupational liver damage—Aromatic amines; Occupational liver damage—Aromatic halogenated hydrocarbons; Occupational liver damage—Aromatic Hydrocarbons; Occupational liver damage—Arsenic; Occupational liver damage—Arsine; Occupational liver damage—Benzene; Occupational liver damage—Benzyl chloride; Occupational liver damage—Beryllium; Occupational liver damage—Beta-Propiolactone; Occupational liver damage—Bipyridyl pesticides; Occupational liver damage—Bismuth; Occupational liver damage—Boron; Occupational liver damage—Boron hydrides; Occupational liver damage—Bromide; Occupational liver damage—Cadmium; Occupational liver damage—Carbolic Acids and Anhydrides; Occupational liver damage—Carbon Disulfide; Occupational liver damage—Carbon tetrachloride; Occupational liver damage—Carbonyls (metal); Occupational liver damage—Chlorinated benzenes; Occupational liver damage—Chlorinated naphthalenes; Occupational liver damage—Chlorodiphenyls and derivatives; Occupational liver damage—Chloroform; Occupational liver damage—Chloroprene; Occupational liver damage—Chromium; Occupational liver damage—Copper; Occupational liver damage—Cresol; Occupational liver damage—Cyclopropane; Occupational liver damage—Dibromochloropropane; Occupational liver damage—Dimethyl sulfate; Occupational liver damage—Dimethylnitrosamine; Occupational liver damage—Dinitrobenzene; Occupational liver damage—Dinitrophenol; Occupational liver damage—Dinitrotoluene; Occupational liver damage—Diphenyl; Occupational liver damage—Ethanolamines; Occupational liver damage—Ethyl Acetate; Occupational liver damage—Ethyl alcohol; Occupational liver damage—Ethyl Ether; Occupational liver damage—Ethyl Salicylate; Occupational liver damage—Ethylene chlorohydrin; Occupational liver damage—Ethylene Dibromide; Occupational liver damage—Ethylene dichloride; Occupational liver damage—Ethylene oxide; Occupational liver damage—Ethylenediamine; Occupational liver damage—Germanium; Occupational liver damage—Hydrazine and derivatives; Occupational liver damage—Hydrogen bromides; Occupational liver damage—Hydrogen Cyanide; Occupational liver damage—Ionizing radiation; Occupational liver damage—Iron; Occupational liver damage—Isopropyl acetate; Occupational liver damage—Kepone pesticides; Occupational liver damage—Mercaptans; Occupational liver damage—Methyl acetate; Occupational liver damage—Methyl Bromide; Occupational liver damage—Methyl Chloride; Occupational liver damage—Methylene chloride; Occupational liver damage—Methylene dianiline; Occupational liver damage—N-butyl acetate; Occupational liver damage—n-Heptane; Occupational liver damage—N-N-Dimethylacetamide; Occupational liver damage—N-Nitrosodimethylamine; Occupational liver damage—N-propyl acetate; Occupational liver damage—N,N-Dimethylformamide; Occupational liver damage—Naphthalene; Occupational liver damage—Naphthol; Occupational liver damage—Nickel; Occupational liver damage—Nitriles; Occupational liver damage—Nitrobenzene; Occupational liver damage—Nitromethane; Occupational liver damage—Nitroparaffins; Occupational liver damage—Nitrophenol; Occupational liver damage—Phenol; Occupational liver damage—Phosphine; Occupational liver damage—Phosphorus; Occupational liver damage—Phthalic Anhydride; Occupational liver damage—Picric Acid; Occupational liver damage—Polybrominated biphenyls; Occupational liver damage—Polychlorinated biphenyls; Occupational liver damage—Propylene dichloride; Occupational liver damage—Pyridine; Occupational liver damage—Pyrogallol; Occupational liver damage—Selenium; Occupational liver damage—Stibine; Occupational liver damage—Styrene/ethyl benzene; Occupational liver damage—Tetrachloroethane; Occupational liver damage—Tetrachloroethylene; Occupational liver damage—Tetramethylthiuram disulfide; Occupational liver damage—Tetryl; Occupational liver damage—Thallium; Occupational liver damage—Thallium sulfate pesticides; Occupational liver damage—Thorium dioxide; Occupational liver damage—Tin; Occupational liver damage—Toluene; Occupational liver damage—Trichloroethylene; Occupational liver damage—Trinitrotoluene; Occupational liver damage—Turpentine; Occupational liver damage—Uranium; Occupational liver damage—Vinyl Chloride; Occupational liver damage—Whole body vibration; Occupational liver damage—Xylene; Occupational metal-induced liver damage—Antimony; Occupational metal-induced liver damage—Arsenic; Occupational metal-induced liver damage—Barium; Occupational metal-induced liver damage—Beryllium; Occupational metal-induced liver damage—Bismuth; Occupational metal-induced liver damage—Boranes; Occupational metal-induced liver damage—Boron; Occupational metal-induced liver damage—Cadmium; Occupational metal-induced liver damage—Chromium; Occupational metal-induced liver damage—Cobalt; Occupational metal-induced liver damage—Copper; Occupational metal-induced liver damage—Germanium; Occupational metal-induced liver damage—Gold; Occupational metal-induced liver damage—Hafnium; Occupational metal-induced liver damage—Halides; Occupational metal-induced liver damage—Hydrazines; Occupational metal-induced liver damage—Iron; Occupational metal-induced liver damage—Lanthanides; Occupational metal-induced liver damage—Lead; Occupational metal-induced liver damage—

Manganese; Occupational metal-induced liver damage—Mercury; Occupational metal-induced liver damage—Molybdenum; Occupational metal-induced liver damage—Nickel; Occupational metal-induced liver damage—Niobium; Occupational metal-induced liver damage—Phosphorus; Occupational metal-induced liver damage—Selenium; Occupational metal-induced liver damage—Tellurium; Occupational metal-induced liver damage—Thallium; Occupational metal-induced liver damage—Tin; Plant toxin-induced liver damage—Albitocin; Plant toxin-induced liver damage—Cycasin; Plant toxin-induced liver damage—Icterogenin; Plant toxin-induced liver damage—Indospicine; Plant toxin-induced liver damage—Lanthana; Plant toxin-induced liver damage—Ngaione; Plant toxin-induced liver damage—Nutmeg; Plant toxin-induced liver damage—Pyrrolidizine; Plant toxin-induced liver damage—Safrole; Plant toxin-induced liver damage—Tannic Acid; Psychotropic agent-induced liver damage; Psychotropic agent-induced liver damage—Benzodiazepine; Psychotropic agent-induced liver damage—Butyrophenone; Psychotropic agent-induced liver damage—monoamine oxidase inhibitors; Psychotropic agent-induced liver damage—Phenothiazines; Psychotropic agent-induced liver damage—Thioxanthene; Psychotropic agent-induced liver damage—tricyclic antidepressant; Anesthetic agent-induced liver damage; Anesthetic agent-induced liver damage—Chloroform; Anesthetic agent-induced liver damage—Cyclopropane; Anesthetic agent-induced liver damage—Ether; Anesthetic agent-induced liver damage—Halothane; Anesthetic agent-induced liver damage—Methoxyflurane; Anesthetic agent-induced liver damage—Nitrous Oxide; Antibiotics-induced liver damage; Antibiotics-induced liver damage—Cephalosporin; Antibiotics-induced liver damage—Chloramphenicol; Antibiotics-induced liver damage—Clindamycin; Antibiotics-induced liver damage—Erythromycin estolate; Antibiotics-induced liver damage—Erythromycin Ethyl succinate; Antibiotics-induced liver damage—Novobiocin; Antibiotics-induced liver damage—Quinolone; Antibiotics-induced liver damage—Spectinomycin; Antibiotics-induced liver damage—Sulfones; Antibiotics-induced liver damage—Telithromycin; Antibiotics-induced liver damage—Tetracycline; Antibiotics-induced liver damage—Nitrofuran; Antibiotics-induced liver damage—Penicillin; Antibiotics-induced liver damage —Rifampicin; Anticonvulsive-induced liver damage; Anticonvulsive-induced liver damage—Mephenytoin; Anticonvulsive-induced liver damage—Phenobarbital; Anticonvulsive-induced liver damage—Phenytoin; Anticonvulsive-induced liver damage—Valproic Acid; Antidiarrheal agent poisoning; Antifungal agent-induced liver damage; Antifungal agent-induced liver damage—5-Fluorocytosine; Antifungal agent-induced liver damage—Amphotericin; Antifungal agent-induced liver damage—Griseofulvin; Antifungal agent-induced liver damage—Ketoconazole; Antifungal agent-induced liver damage—Saramycetin; Antimetazoal agent-induced liver damage; Antimetazoal agent-induced liver damage—Amodiaquine; Antimetazoal agent-induced liver damage—Hycanthone; Antiprotozoal agent-induced liver damage; Antiprotozoal agent-induced liver damage—8-Hydroxyquinolone; Antiprotozoal agent-induced liver damage—Carbarsone; Antiprotozoal agent-induced liver damage—Emetine; Antiprotozoal agent-induced liver damage—Mepacrine; Antiprotozoal agent-induced liver damage—Metronidazole; Antiprotozoal agent-induced liver damage—Thiabendazole; Antituberculous agent-induced liver damage; Antituberculous agent-induced liver damage—Cycloserine; Antituberculous agent-induced liver damage—Ethionamide; Antituberculous agent-induced liver damage—Isoniazid; Antituberculous agent-induced liver damage—p-aminosalicylic acid; Antituberculous agent-induced liver damage—Rifampicin; Antiviral agent-induced liver damage; Antiviral agent-induced liver damage—Cytarabine; Antiviral agent-induced liver damage—idoxuridine; Antiviral agent-induced liver damage—Vidarabine; Antiviral agent-induced liver damage—xenylamine; Mycotoxin-induced liver damage—Aflatoxin; Mycotoxin-induced liver damage—Cyclochlorotine; Mycotoxin-induced liver damage—Luteoskyrins; Mycotoxin-induced liver damage—Ochratoxin; Mycotoxin-induced liver damage—Rubratoxin; Mycotoxin-induced liver damage—Sterigmatocystin; Endocrine agent-induced liver damage; Endocrine agent-induced liver damage—Anabolic C-17; Endocrine agent-induced liver damage—Antithyroid drugs; Endocrine agent-induced liver damage—Glucocorticoids; Endocrine agent-induced liver damage—Oral contraceptives; Endocrine agent-induced liver damage—Oral hypoglycemics; Endocrine agent-induced liver damage—Steroids; Endocrine agent-induced liver damage—Tamoxifen; Metastatic liver cancer; Heptaosplenic T-cell Lymphoma; Childhood liver cancer, primary; Angiosarcoma of the liver; Idiopathic liver cirrhosis; Drug-induced liver disease; Liver vein outflow obstruction; Liver fibrosis; Fatty liver disease; Hepatitis G; Chronic Hepatitis; Hepatocellular jaundice; Cirrhosis of liver; Postoperative Jaundice; Obstructive Jaundice; End Stage Liver Failure; Andersen disease; Type IV Glycogen Storage Disease; Type III Glycogen Storage Disease; Type I Glycogen Storage Disease; Von Gierke disease IA; Von Gierke disease IB; Von Gierke Disease; Fanconi-Bickel syndrome; Type 0 Glycogen Storage Disease; Breast Milk Jaundice; Malignant Jaundice; Chronic liver disease like bleeding tendencies; Hepatic encephalopathy like coma; Hepatosplenomegaly; Glycogen Storage Disease Type I; Cholestasis—lymphoedema, syndrome; Aagenaes syndrome; Occasional hepatitis; Mild jaundice; Glycogen Storage Disease IXb; Glycogen Storage Disease IXa1; Glycogen Storage Disease IXc; Glycogen storage diseases; Glycogen storage disease type 6; Glycogen storage disease type 1C; Glycogen storage disease type 1D; Hepatotoxicity; Short stature cranial hyperostosis hepatomegaly diabetes; Cholestasis; Renal-hepatic-pancreatic dysplasia—Dandy Walker cyst; Hypoglossia with Situs Inversus; Acute fatty liver of pregnancy; Hepatic amyloidosis with intrahepatic cholestasis; Hepatitis X (non-A,-B,-C,-D,-E); Bile acid synthesis defects; Bile acid synthesis defects, congenital, 1; Bile acid synthesis defects, congenital, 2; Bile acid synthesis defects, congenital, 3; Bile acid synthesis defects, congenital, 4; Bile plug syndrome; Malabsorption due to bile acid synthesis defects, idiopathic; Bile acid synthesis defect, congenital, 2; Bile acid synthesis defect, congenital, 4; Bile ducts paucity, non syndromic form; Bile duct paucity, non syndromic form; Bile duct paucity in Liver Allograft Rejection; Lipoatrophy with diabetes, hepatic steatosis, cardiomyopathy, and leukomelanodermic papules; Short stature, cranial hyperostosis, hepatomegaly and diabetes; Diabetes, neonatal—congenital hypothyroidism—congenital glaucoma—hepatic fibrosis—polycystic kidneys; Arthrogryposis—renal dysfunction—cholestasis syndrome; Addison-Gull syndrome; Reye's Syndrome; Hyperpigmentation, Cutaneous, With Hypertrichosis, Hepatosplenomegaly, Heart Anomalies, Hearing Loss, And Hypogonadism; Hepatic encephalopathy syndrome; Cirrhotic cardiomyopathy; Cholestatic jaundice—renal tubular insufficiency; Congenital hepatic fibrosis; Nephronophthisis—hepatic fibrosis; Polycystic liver disease; Biliary atresia, intrahepatic, non syndromic form;

Hypoglycemia with deficiency of glycogen synthetase in the liver; Hepatocellular carcinoma (fibrolamellar variant); Biliary atresia, intrahepatic, syndromic form; Cholestasis, progressive familial intrahepatic 1; Cholestasis, progressive familial intrahepatic 2; Cholestasis, progressive familial intrahepatic 3; Benign intrahepatic cholestasis type 1; Benign intrahepatic cholestasis type 2; Cholestasis, Intrahepatic; Cholestasis disease of pregnancy; Cholestasis, intrahepatic of pregnancy; Cholestasis—pigmentary retinopathy—cleft palate; Pyruvate kinase deficiency, liver type; Carnitine palmitoyl transferase II deficiency, infantile hepatocardiomuscular type; Clonorchiasis; Intrahepatic cholangiocarcinoma; Hepatorenal tyrosinemia; Oculocutaneous tyrosinemia; Congenital hepatic *porphyria; Porphyria*; Neoplastic *porphyria tarda*; Cerebellar vermis hypoplasia—oligophrenia—congenital ataxia—coloboma—hepatic fibrosis; Nodular regenerative hyperplasia of the liver; Bantu siderosis; Megarbane-Jalkh Syndrome; Hepatic cystic hamartoma; Obliterative portal venopathy; Pearson's marrow-pancreas syndrome; Liver disease—retinitis pigmentosa—polyneuropathy—epilepsy; Acute cholinergic dysautonomia; Acute liver failure; Acute myelofibrosis; Acute panmyelosis; Congenital nonhemolytic jaundice; Cirrhosis, familial; Asparatate aminotransferase elevation; Hepatorenal Syndrome; Hepatic fibrosis, congenital; Neonatal hepatitis; Hepatic Venoocclusive Disease with immunodeficiency; Hepatic veno-occlusive disease—immunodeficiency; Crigler-Najjar syndrome, type 1; Crigler-Najjar syndrome, type 2; Crigler-Najjar Syndrome; Hepatoblastoma; Short stature—cranial hyperostosis—hepatomegaly; Meckel syndrome type 2; Meckel Syndrome; Meckel syndrome type 3; Meckel syndrome, type 5; Portal hypertension due to intrahepatic block; Non-alcoholic steatohepatitis (NASH); Dykes-Markes-Harper syndrome; Unusual facies, hepatic fibrosis, renal cysts and mental retardation; Leigh syndrome, Saguenay-Lac-St. Jean type; Renal dysplasia hepatic fibrosis dandy walker; Dubin-Johnson Syndrome; Alpha 1-Antitrypsin Deficiency; Byler Disease; Mulibrey Nanism syndrome; Alagille Syndrome; *Caroli* Disease; MULIBREY Nanism; NASH syndrome; Saguenay-Lac Saint Jean—COX deficiency; Cirrhosis-like flapping tremens; Dyck Syndrome; Sarrouy disease; Stauffer syndrome; Stuart-Bras disease; Zieve syndrome; PFIC; Summerskill-Walshe-Tygstrup syndrome; Hanot-MacMahon-Thannhauser syndrome; Havlikova syndrome; Mosse syndrome; Hardikar syndrome; Crawfurd syndrome; Campomelia Cumming type; Hypoplasia hepatic ductular; Bard-Pic syndrome; Aguecheek disease; Bearn-Kunkel syndrome; Bronze baby syndrome; Castellani syndrome; Southwestern Athabaskan genetic diseases; Navajo neurohepatopathy; Reynolds syndrome; Retinohepatoendocrinologic syndrome; Tang Hsi Ryu syndrome; COACH syndrome; Daneman Davy Mancer syndrome; Tricho-hepato-enteric syndrome; Thompson-Baraitser syndrome; Multifocal fibrosclerosis; Baber's syndrome; Ivemark II; Ballard syndrome; Fitz-Hugh-Curtis syndrome; Rotor syndrome; Urioste Martinez-Frias syndrome and Budd-Chiari syndrome.

In one embodiment, the liver condition is high cholesterol, alcoholic liver disease (including acute alcoholic hepatitis), cirrhosis, cysts, primary biliary cirrhosis, fatty liver disease (NAFLD), fibrosis, jaundice, primary sclerosing cholangitis (PSC), hemochromatosis, primary biliary cirrhosis, Alpha-1 Antitrypsin Deficiency or drug induced liver injury (e.g. caused by antimicrobials, cardiovascular, CNS agents, antineoplastic and analgesic (acetaminophen). See *Am J Gastroenterol* 2014; 109:950-966; doi:10.1038/ajg.2014.131; published online 17 Jun. 2014 which is incorporated by reference.

In one aspect, liver damage is determined by standard liver function tests and or by imaging (CT, X-Ray, MRI etc.). Liver function tests include bilirubin, ammonia, gamma-glutamyl transferase (GGT), alanine aminotransferase (ALT or SGPT), aspartate aminotransferase (AST or SGOT), and alkaline phosphatase (ALP).

Non-Alcoholic Fatty Liver Disease (NAFLD) and Non-Alcoholic Steatohepatitis (NASH)

NAFLD and its more severe form NASH are associated with several diseases (obesity, type 2 diabetes, dyslipidaemia and hypertension), having insulin resistance as the common factor. These conditions cluster to form the insulin resistance or metabolic syndrome, carrying a high risk for cardiovascular complications. NASH itself, as well as pure fatty liver, is an insulin-resistant state, not only in subjects with additional metabolic disorders, but also in lean subjects.

Because the histopathology of NASH resembles that of alcohol-induced steatohepatitis (ASH), these 2 conditions share common pathogenic aspects. Immunological mechanisms play a pivotal role in the pathogenesis of ASH. This has been well demonstrated by studies of patients and experimental animals. In hospitalized patients with severe ASH and NASH, serum levels of several pro-inflammatory cytokines, including TNF-α, are increased significantly. Cytokine levels correlate well with liver disease severity.

While it is widely acknowledged that TNF-α expression increases in obesity, the mechanisms driving chronic overproduction of TNF-α in obese humans remain obscure. However, the resultant chronic inflammatory state has been implicated in the pathogenesis of the metabolic syndrome that often accompanies obesity. The immunopathogenesis of obesity-related NASH has been studied extensively in the ob/ob mice model. The studies clearly demonstrate that cytokine producing cells in ob/ob livers are Th1 polarized. This microenvironment favours the perpetuation of inflammatory signals. Inhibiting TNFα significantly reduced the hepatic activities of both kinases, thereby supporting the concept that excessive TNFα activity contributes to hepatic insulin resistance in leptin-deficient mice. A strong positive correlation has been noted between hepatic insulin resistance and NASH in many experimental animals and humans.

NAFLD and NASH are initially suspected if blood tests show high levels of liver enzymes. An ultrasound is typically used to confirm the NAFLD diagnosis.

In one aspect, in the uses and methods as described herein the NASH or NAFLD patient may be treated orally with the compounds of the present description may be used in order to prevent, control or reduce liver damage.

In one aspect, in the uses and methods as described herein the patient is a NASH or NAFLD patient that has developed cirrhosis.

In one aspect, in the uses and methods as described herein the NASH or NAFLD patient is overweight or obese, has diabetes, high cholesterol or high triglycerides.

High Cholesterol

High blood cholesterol levels are associated with increased risk of suffering from heart attack and stroke.

In one aspect, the patient is a patient having elevated blood cholesterol levels.

In one aspect, an elevated cholesterol level is a total blood cholesterol level that exceeds 200 mg/dL, that exceeds 220 mg/dL or that exceeds 240 mg/dL.

Alcoholic Liver Disease (ALD)

Alcoholic liver disease occurs after years of heavy drinking. Alcohol can cause inflammation in the liver. ALD has three stages: 1) alcoholic fatty liver disease; 2) alcoholic hepatitis and 3) Cirrhosis.

Alcoholic hepatitis (not related to infectious hepatitis) is the second, more serious stage of ALD. It occurs when alcohol misuse over a longer period causes the tissues of the liver to become inflamed.

Damage caused by alcoholic fatty liver disease or Alcoholic hepatitis can usually be reversed if the use of alcohol is stopped.

Cirrhosis is the final stage of alcohol-related liver disease, which occurs when the liver becomes significantly scarred. Cirrhosis is generally not reversible, but stopping drinking alcohol can prevent further damage and significantly increase life expectancy.

In one aspect the ALD is diagnosed with blood test, liver biopsy or imagery (ultrasound scan, computerised tomography (CT) scan).

In one aspect, in the uses and methods as described herein the ALD patient may be treated with the compounds of the present description to prevent, control or reduce liver damage.

Cirrhosis

Cirrhosis is scarring of the liver caused by many forms of liver diseases and conditions, such as hepatitis and chronic alcohol abuse.

In one aspect the ALD is diagnosed with blood test, liver biopsy or imagery (ultrasound scan, computerised tomography (CT) scan).

In one aspect, in the uses and methods as described herein the cirrhosis patient may be treated with the compounds of the present description in order to prevent, control or reduce liver damage.

Cysts

Cysts are thin-walled structures that contain fluid. Most cysts are single, although some patients may have several. The symptoms associated with liver cysts include upper abdominal fullness, discomfort, or pain.

The cysts are usually found by ultrasound (US) or computed tomography (CT scan).

In one aspect, in the uses and methods as described herein the cysts patient may be treated with the compounds of the present description in order to prevent, control or reduce the cysts and/or the symptoms associated with liver cysts.

Fibrosis

Liver fibrosis is the scarring process that represents the liver's response to injury.

Liver fibrosis is usually found by biopsy.

In one aspect, in the uses and methods as described herein the liver fibrosis patient may be treated with the compounds of the present description in order to prevent, reduce or control liver fibrosis or inflammation associated/caused by liver fibrosis.

Intra-Hepatic or Post-Hepatic Jaundice

There are three types of jaundice depending on what is causing disruption to the normal removal of bilirubin from the body.

In one aspect, in the uses and methods as described herein the jaundice patient is a patient that suffers from:

intra-hepatic jaundice (also known as hepatocellular jaundice)—the disruption occurs inside the liver. This can be caused by conditions such as Gilbert's syndrome, cirrhosis or other liver damage.

post-hepatic jaundice (also known as obstructive jaundice)—the disruption prevents the bile (and the bilirubin inside it) from draining out of the gallbladder and into the digestive system. This can be caused by conditions such as gallstones or tumours.

In one aspect, in the uses and methods as described herein the intra-hepatic or post-hepatic patient may be treated with the compounds of the present description in order to control, reduce or prevent liver damage.

In one aspect, in the uses and methods as described herein the jaundice patient suffers from intra-hepatic jaundice.

Primary Sclerosing Cholangitis (PSC)

PSC is a disease of the bile ducts. The term "cholangitis" in primary sclerosing cholangitis refers to inflammation of the bile ducts, while the term "sclerosing" describes the hardening and scarring of the bile ducts that result from chronic inflammation.

Primary sclerosing cholangitis is a progressive disease that leads to liver damage and, eventually, liver failure.

In one aspect, in the uses and methods as described herein the PSC patient may be treated with the compounds of the present description in order to reduce, control, or prevent liver damage.

Hemochromatosis

Hemochromatosis is an hereditary condition characterised in an excess on iron absorption. The excess iron is stored in organs, especially liver, heart and pancreas. The excess iron can poison these organs, leading to life-threatening conditions such as cancer, heart arrhythmias and cirrhosis.

In one aspect, in the uses and methods as described herein the PSC patient may be treated with the compounds of the present description in order to control, prevent or reduce liver damage.

Alpha-1 Antitrypsin Deficiency

The genetic defect in alpha1-antitrypsin (AAT) deficiency alters the configuration of the alpha1-antitrypsin molecule and prevents its release from hepatocytes. As a result, serum levels of alpha1-antitrypsin are decreased, leading to low alveolar concentrations, where the alpha1-antitrypsin molecule normally would serve as protection against antiproteases. The resulting protease excess in alveoli destroys alveolar walls and causes emphysema. The accumulation of excess alpha1-antitrypsin in hepatocytes can also lead to destruction of these cells and ultimately, clinical liver disease.

In one aspect, in the uses and methods as described herein the AAT patient may be treated orally with the compounds of the present description in order to prevent, control or reduce liver damage.

Primary Biliary Cirrhosis (PBC)

PBC is a slow, chronic liver disease which can cause progressive destruction of the bile ducts in the liver. The body attacks the cells lining the bile ducts within the liver as if they are foreign to the body itself. This damage causes poor drainage of bile acids, which leak outwards and damage the normal liver cells. This causes inflammation and scarring which may, after many years become extensive. This widespread damage and scarring is commonly called cirrhosis.

PBC usually diagnosed with blood tests. The presence of AMA (antimitochondrial antibody) is indicative of PBC.

In one aspect, in the uses and methods as described herein the PBC patient may be treated with the compounds of the present description in order to prevent, control or reduce liver damage.

In one aspect, in the uses and methods as described herein the PBC patient has tested positive for AMA.

Sepsis

Sepsis is a potentially life-threatening complication of an infection. Sepsis occurs when endotoxins such as LPS are released into the bloodstream, triggering an inflammatory response throughout the body. This inflammation can trigger a cascade of changes that can damage multiple organ systems, causing them to fail. If sepsis progresses to septic shock, blood pressure drops dramatically, which may lead to death.

In one aspect, the compounds of the present description may be used to treat sepsis.

In one aspect, in the uses and methods as described herein the sepsis patient may be treated with the compounds of the present description in order to prevent, control or reduce the risks associated to a septic shock.

Formulations

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "patient or subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

In some embodiments, the therapeutically effective amount of a compound as defined herein, or a pharmaceutically acceptable salt thereof, can be administered to a patient alone or admixed with a pharmaceutically acceptable carrier.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of the present description that, upon administration to a recipient, is capable of providing, either directly or indirectly, a compound of the present description or an inhibitory active metabolite or residue thereof.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled.

Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of the present description with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of the present description include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of the present description. Additionally, the description contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promotors to enhance bioavailability, fluorocarbons, and/or other conventional solubilizing or dispersing agents.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration. Provided compositions may be formulate such that a dosage of between 0.01-100 mg/kg body weight/day of the inhibitor can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Compounds or compositions described herein may be administered using any amount and any route of administration effective for treating or lessening the severity of the disorders or diseases as contemplated herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Combinations

Depending upon the particular condition, or disease, to be treated, additional therapeutic agents that are normally administered to treat that condition may also be present in the compositions of this disclosure or administered separately as a part of a dosage regimen. As used herein, additional therapeutic agents that are normally administered to treat a particular disease, or condition, are known as "appropriate for the disease, or condition, being treated."

In some embodiments, the composition of a compound or compounds described herein can be in combination with an additional therapeutic agent.

It will be understood, however, that the total daily usage of the compounds and compositions of the present description will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of the present description administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present description comprise administration to a patient in need of such treatment from about 10 mg to about 1000 mg of the compound(s) of the present description per day in single or multiple doses.

As used herein, the term "combination," "combined," and related terms refers to the simultaneous or sequential administration of therapeutic agents in accordance with the present description. For example, a provided compound may be administered with another therapeutic agent simultaneously or sequentially in separate unit dosage forms or together in a single unit dosage form. Accordingly, an embodiment of the present description provides a single unit dosage form comprising a provided compound, an additional therapeutic agent, and a pharmaceutically acceptable carrier, adjuvant, or vehicle for use in the methods of the present description.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions should be formulated such that a dosage of between 0.01-100 mg/kg body weight/day of a provided compound can be administered.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent. In such compositions a dosage of between 0.01-1,000 g/kg body weight/day of the additional therapeutic agent can be administered.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Provided compounds, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a provided compound. Implantable devices coated with a compound of the present description are another embodiment of the present description.

In another aspect, the present description provides a method of method of synthesizing a compound of any of the formulae herein. Another embodiment is a method of making a compound of any of the formulae herein using any one, or combination of, reactions delineated herein. The method can include the use of one or more intermediates or chemical reagents delineated herein.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Definitions

As used herein, the singular forms "a", "an" and "the" are intended to include the plural forms as well, unless the context clearly indicates otherwise. To the extent that the terms "including", "includes", "having", "has", "with", or variants thereof are used in either the description and/or the claims, such terms are intended to be inclusive in a manner similar to the term "comprising."

The term "about" or "approximately" means within an acceptable error range for the particular value as determined by a person skilled in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Definitions of specific functional groups and chemical terms are described in more detail below. For purposes of the present description, the chemical elements are identified in accordance with the Periodic Table of the Elements, CAS version, Handbook of Chemistry and Physics, 75$^{th}$, Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$, Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the present description. Unless otherwise stated, all tautomeric forms of the compounds are within the scope of the present description. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of the present description. Such compounds are useful, for example, as analytical tools, as probes in biological assays, or as therapeutic agents in accordance with the present description.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., Enantiomers, Racemates and Resolutions (Wiley Interscience, New York, 1981); Wilen, et al., Tetrahedron 33:2725 (1977); Eliel, E. L. Stereochemistry of Carbon Compounds (McGraw-Hill, N Y, 1962); Wilen, S. H. Tables of Resolving Aqents and Optical Resolutions, p. 268 (E. L. Eliel, Ed., Univ. of Notre Dame Press, Notre Dame, Ind. 1972).

The synthesized compounds may be separated from a reaction mixture and further purified by a method such as column chromatography, high pressure liquid chromatography, or recrystallization. Synthetic chemistry transformations and protecting group methodologies (protection and deprotection) useful in synthesizing the compounds described herein include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reaqents for Organic Synthesis, John Wiley and Sons (1994); and L. Paquette, ed., Encyclopedia of Reaqents for Organic Synthesis, John Wiley and Sons (1995), and subsequent editions thereof.

The term "$C_{m-n}$" or "$C_{m-n}$ group" used alone or as a prefix, refers to any group having m to n carbon atoms.

The term "alkyl" represents a linear, branched or cyclic hydrocarbon moiety. The terms "alkenyl" and "alkynyl" represent a linear, branched or cyclic hydrocarbon moiety which has one or more double bonds or triple bonds in the chain. Examples of alkyl, alkenyl, and alkynyl groups include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, allyl, vinyl, acetylenyl, ethylenyl, propenyl, isopropenyl, butenyl, isobutenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl, hexynyl, cyclopropyl, cyclobutyl, cyclopentyl, cyclohexenyl, cyclohexdienyl and cyclohexyl.

Where indicated the "alkyl," "alkenyl," and "alkynyl" can be optionally substituted such as in the case of haloalkyls in which one or more hydrogen atom is replaced by a halogen, e.g. an alkylhalide. Examples of haloalkyls include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl. Aside from halogens, where indicated, the alkyl, alkenyl or alkynyl groups can also be optionally substituted by, for example, oxo, —$NR_dR_e$, —$CONR_dR_e$, =$NO$—$R_e$, —$NR_dCOR_e$, carboxy, —$C(=NR_d)NR_eR_f$, azido, cyano, $C_{1-6}$ alkyloxy, $C_{2-6}$ alkenyloxy, $C_{2-6}$ alkynyloxy, —$N(R_d)C(=NR_e)$—$NR_fR_g$, hydroxyl, nitro, nitroso, —$N(R_h)CONR_iR_j$, —$S(O)_{0,2}R_a$, —$C(O)R_a$, —$C(O)OR_a$, —$SO_2NR_aR_b$, —$NR_aSO_2R_b$, —$NR_aSO_2NR_bR_c$, —$CR_aN$=$OR_a$, and/or —$NR_aCOOR_b$, wherein $R_a$-$R_j$ are each independently H, $C_{1-4}$ alkyl, $C_{2-4}$ alkenyl, or $C_{2-4}$ alkynyl. The "alkyl," "alkenyl," and "alkynyl" can also be optionally substituted by —$OCONR_eR_f$. The "alkyl," "alkenyl," and "alkynyl" can also be optionally substituted by —$OCONR_eR_f$. The "alkyl," "alkenyl," and "alkynyl" can also be optionally substituted by —$C(=S)NR_dR_e$.

As used herein, an "alkylsulfonate" comprises an alkyl, alknenyl or alkynyl moiety linked to a sulfonate group:

alkyl-S(O)$_2$O—, alkenyl-S(O)$_2$O— or alkynyl-S(O)$_2$O—. Where indicated, the alkyl, alknenyl or alkynyl can be substituted.

The term "aryl" represents a carbocyclic moiety containing at least one benzenoid-type ring (i.e., may be monocyclic or polycyclic), and where indicated may be optionally substituted with one or more substituents.

Examples include but are not limited to phenyl, tolyl, dimethylphenyl, aminophenyl, anilinyl, naphthyl, anthryl, phenanthryl or biphenyl. The aryl groups can be optionally substituted by, for example, halogens, NR$_d$R$_e$, —CONR$_d$R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{1-6}$ alkyloxy, C$_{2-6}$ alkenyloxy, C$_{2-6}$ alkynyloxy, —S(O)$_{0-2}$R$_a$, optionally substituted 5-12 member heteroaryl, optionally substituted 6-18 member heteroaralkyl, optionally substituted 3-12 member heterocycle, optionally substituted 4-18 member heterocycle-alkyl, —C(O)R$_a$, —C(O)OR$_a$, —SO$_2$NR$_a$R$_b$, —NR$_a$SO$_2$R$_b$, —NR$_a$SO$_2$NR$_b$R$_c$, —CR$_a$N=OR$_b$, and/or —NR$_a$COOR$_b$, wherein R$_a$-R$_j$ are each independently H, C$_{1-4}$ alkyl, C$_{2-4}$ alkenyl, or C$_{2-4}$ alkynyl. The aryl group can also be optionally substituted by —OCONR$_e$R$_f$. The aryl group can also be optionally substituted by —C(=S)NR$_d$R$_e$.

As used herein, an "arylsulfonate" comprises an aryl moiety linked to a sulfonate group: (aryl-S(O)$_2$O—). Where indicated, the aryl can be substituted.

The term "heterocycle" represents an optionally substituted, non aromatic, saturated or partially saturated wherein said cyclic moiety is interrupted by at least one heteroatom selected from oxygen (O), sulfur (S) or nitrogen (N). Heterocycles may be monocyclic or polycyclic rings. For example, a 3-12 member heterocycle is an optionally substituted, non aromatic, saturated or partially saturated cyclic moiety having 3-12 ring atoms wherein at least one ring atom is a heteroatom selected from oxygen (O), sulfur (S) or nitrogen (N). Examples include but are not limited to azetidinyl, dioxolanyl, morpholinyl, morpholino, oxetanyl, piperazinyl, piperidyl, piperidino, cyclopentapyrazolyl, cyclopentaoxazinyl, cyclopentafuranyl, tetrahydrofuranyl, tetrahydrothiofuranyl, tetrahydrothiofuranyl, tetrahydropyranyl, tetrahydrothiopyranyl, tetrahydrothiopyranyl dioxyde, thiazolinyl, oxazolinyl, pyranyl, thiopyranyl, aziridinyl, azepinyl, dioxazepinyl, diazepinyl, oxyranyl, oxazinyl, pyrrolidinyl, thiopyranyl, thiolane, pyrazolidinyl, dioxanyl, and imidazolidinyl. Where indicated, the heterocyclic groups can be optionally substituted by, for example, halogens, oxo, —NR$_d$R$_e$, CONR$_d$R$_e$, =NO—R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{7-12}$ aralkyl, C$_{6-12}$ aryl, C$_{1-6}$ alkyloxy, C$_{2-6}$ alkenyloxy, C$_{2-6}$ alkynyloxy, —S(O)$_{0-2}$R$_a$, C$_{6-10}$ aryl, C$_{7-10}$ aryloxy, C$_{7-10}$ arylalkyl, C$_{6-10}$aryl-C$_{1-10}$alkyloxy, —C(O)R$_a$, =C(O)OR$_a$, —SO$_2$NR$_a$, —NR$_a$SO$_2$R$_b$, —NR$_a$SO$_2$NR$_b$R$_c$, —CR$_a$N=OR$_b$, and/or —NR$_a$COOR$_b$, wherein R$_a$-R$_j$ are each independently H, C$_{1-4}$ alkyl, C$_{2-4}$ alkenyl or C$_{2-4}$ alkynyl. The heterocyclic groups can also be optionally substituted by —OCONR$_e$R$_f$. The heterocyle group can also be optionally substituted by —C(=S)NR$_d$R$_e$.

The term "heterocycle-alkyl" represents an optionally substituted heterocycle group attached to the adjacent atom by an alkyl, alkenyl, or alkynyl group. It is understood that in a 5-18 member heterocycle-alkyl moiety, the term "5-18 member" represents the total number of ring atoms present in the heterocycle moiety and carbon atoms present in the alkyl, alkenyl or alkynyl portion. Where indicated the heterocycle-alkyl groups can be optionally substituted by, for example, halogens, oxo, —NR$_d$R$_e$, —CONR$_d$R$_e$, —C(=S)NR$_d$R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_a$R$_b$, C$_{1-6}$ alkyl, C$_{2-6}$ alkenyl, C$_{2-6}$ alkynyl, C$_{1-6}$ alkyloxy, C$_{2-6}$ alkenyloxy, C$_{2-6}$ alkynyloxy, —S(O)$_{0-2}$R$_a$, C$_{6-10}$ aryl, C$_{6-10}$ aryloxy, C$_{7-10}$ arylalkyl, C$_{6-10}$ aryl-C$_{1-10}$ alkyloxy, —C(O)R$_a$, —C(O)OR$_a$, =NO—R$_e$, —SO$_2$NR$_a$R$_b$, —NR$_a$SO$_2$R$_b$, —NR$_a$SO$_2$NR$_b$R$_c$, —CR$_a$N=OR$_b$, and/or —NR$_a$COOR$_b$, wherein R$_a$-R$_j$ are each independently H, C$_{1-4}$ alkyl, C$_{2-4}$ alkenyl or C$_{2-4}$ alkynyl. The heterocycle-alkyl groups can also be optionally substituted by —OCONR$_e$R$_f$. The heterocycle-alkyl can also be optionally substituted by —C(=S)NR$_d$R$_e$.

The term "heteroaryl" represents an optionally substituted aromatic cyclic moiety wherein said cyclic moiety is interrupted by at least one heteroatom selected from oxygen (O), sulfur (S) or nitrogen (N). Heteroaryls may be monocyclic or polycyclic rings. For example, a 5-12 member heteroaryl is an optionally substituted, aromatic cyclic moiety having 5-12 ring atoms wherein at least one ring atom is a heteroatom selected from oxygen (O), sulfur (S) or nitrogen (N). Examples include but are not limited to—dithiadiazinyl, furanyl, isooxazolyl, isothiazolyl, imidazolyl, oxadiazolyl, dioxazole, oxatriazole, oxazolyl, pyrazinyl, pyridazinyl, pyrimidinyl, pyridyl, pyrazolyl, pyrrolyl, thiatriazolyl, tetrazolyl, thiadiazolyl, triazolyl, thiazolyl, thienyl, tetrazinyl, thiadiazinyl, triazinyl, thiazinyl, furoisoxazolyl, imidazothiazolyl, thienoisothiazolyl, thienothiazolyl, imidazopyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, benzoxazinyl, benzothiazinyl, quinazolinyl, naphthyridinyl, quinolinyl, isoquinolinyl, benzopyranyl, pyridopyridazinyl and pyridopyrimidinyl. Where indicated the heteroaryl groups can be optionally substituted by, for example, halogens, —NR$_d$R$_e$, —CONR$_d$R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{1-6}$ alkyloxy, C$_{2-6}$ alkenyloxy, C$_{2-6}$ alkynyloxy, —S(O)$_{0-2}$R$_a$, C$_{6-10}$ aryl, C$_{6-10}$ aryloxy, C$_{7-10}$ arylalkyl, C$_{6-10}$aryl-C$_{1-10}$alkyloxy, —C(O)R$_a$, —C(O)OR$_a$, —SO$_2$NR$_a$R$_b$, —NR$_a$SO$_2$R$_b$, N—R$_a$SO$_2$NR$_b$R$_c$—CR$_a$N=OR$_b$, and/or —NR$_a$COOR$_b$, wherein R$_a$-R$_j$ are each independently H, C$_{1-4}$ alkyl, C$_{2-4}$ alkenyl or C$_{2-4}$ alkynyl. The heteroaryl groups can also be optionally substituted by —OCONR$_e$R$_f$. The heteroaryl can also be optionally substituted by —C(=S)NR$_d$R$_e$.

The term "heteroaralkyl" represents an optionally substituted heteroaryl group attached to the adjacent atom by an alkyl, alkenyl, or alkynyl group.

The terms "alkoxy," "alkenyloxy," and "alkynyloxy" represent an alkyl, alkenyl or alkynyl moiety, respectively, which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy and neohexyloxy. The terms "aryloxy," represent an aryl moiety substituted with an oxygen, wherein the point of attachment to the molecule it substitutes is on the oxygen.

The term "haloalkyl" used alone or as a suffix or prefix, refers to a $C_1$-$C_6$ alkyl group substituted by 1 to 3 halogen atoms or fluorine up to the perfluoro level. Examples of such groups include trifluoromethyl, tetrafluoroethyl, 1,2-dichloropropyl, 5-bromopentyl, 6-iodohexyl.

The term "heterocyclic group," "heterocyclic moiety," "heterocyclic," or "heterocyclo" used alone or as a suffix or prefix, refers to a radical derived from a heterocycle by removing one or more hydrogens therefrom.

The term "heterocyclyl" used alone or as a suffix or prefix, refers a monovalent radical derived from a heterocycle by removing one hydrogen therefrom.

The terms "5-membered", "6-membered" and "7-membered" refers to a group having a ring that contains 5, 6 or 7 ring atoms.

In addition to the polycyclic heterocycles described herein, heterocycle includes polycyclic heterocycles wherein the ring fusion between two or more rings includes more than one bond common to both rings and more than two atoms common to both rings.

The term "amine" or "amino" refers to —$NH_2$.

The term "halogen" includes fluorine, chlorine, bromine and iodine.

The term "halogenated," used as a prefix of a group, means one or more hydrogens on the group are replaced with one or more halogens.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl).

As used herein a "direct bond" or "covalent bond" refers to a single, double or triple bond. In certain embodiments, a "direct bond" or "covalent bond" refers to a single bond.

Compounds of formula (I) include pharmaceutically acceptable salts, esters and prodrugs thereof.

the term "pharmaceutically acceptable salt" refers to those salts of the compounds formed by the process of the present description which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66: 1-19 (1977). The salts can be prepared in situ during the final isolation and purification of the compounds of the present description, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present description which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present description which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the description. "Prodrug", as used herein means a compound which is convertible in vivo by metabolic or chemical means (e.g. by hydrolysis) to afford any compound delineated by the formulae of the instant description. Various forms of prodrugs are known in the art, for example, as discussed in Bundgaard, (ed.), *Design of Prodrugs,* Elsevier (1985); Widder, et al. (ed.), *Methods in Enzymology,* vol. 4, Academic Press (1985); Krogsgaard-Larsen, et al., (ed). *"Design and Application of Prodrugs, Textbook of Drug Design and Development"*, Chapter 5, 113-191 (1991); Bundgaard, et al., *Journal of Drug Deliver Reviews,* 8:1-38 (1992); Bundgaard, *J. of Pharmaceutical Sciences,* 77:285 et seq. (1988); Higuchi and Stella (eds.) *Prodrugs as Novel Drug Delivery Systems,* American Chemical Society (1975); and Bernard Testa & Joachim Mayer, *"Hydrolysis In Drug And Prodrug Metabolism: Chemistry, Biochemistry And Enzymology"*, John Wiley and Sons, Ltd. (2002).

BRIEF DESCRIPTION OF THE FIGURES

FIG. 1 represents the ALT levels 6 hours post liver injury induction by GalN/LPS.

FIG. 2 represents the survival at 8 and 23 hours post liver injury induction by GalN/LPS.

FIG. 3 represents ALT Activity, 6 hours post liver injury (Study b).

FIG. 4 ALT Activity, 6 hours post liver injury (Study c).

EXAMPLES

Figure 5:
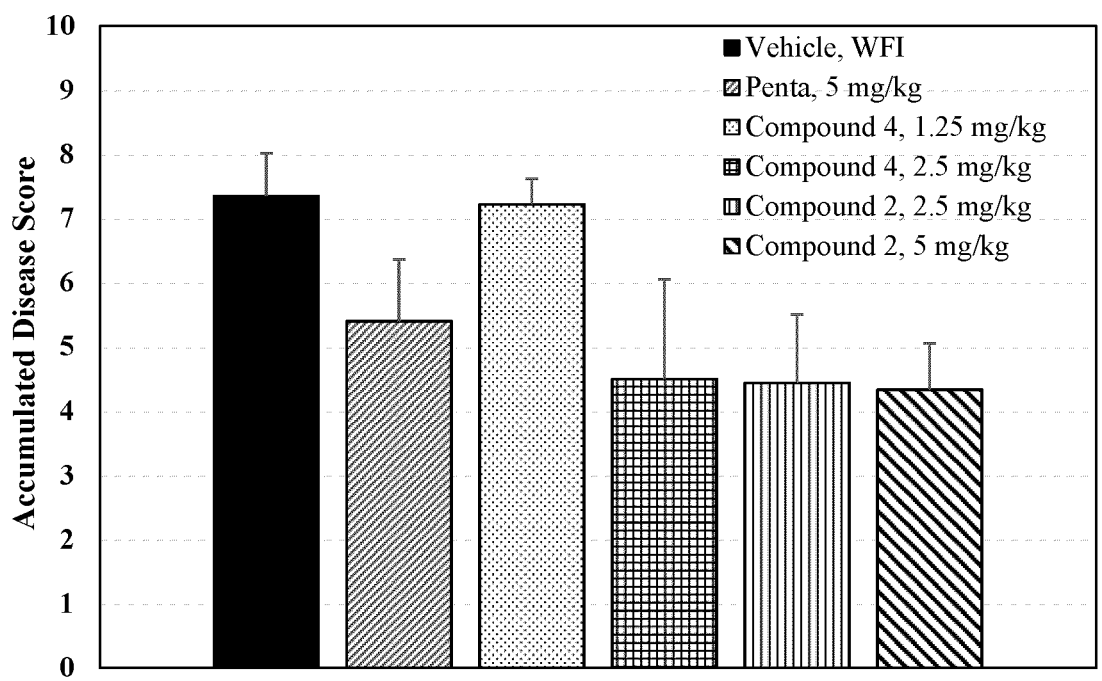
FIG. 5 represents the accumulated disease index at day 7.

As used herein, the following abbreviations may have the following meanings:

| Abbreviation | Term |
| --- | --- |
| AcOH | Acetic acid |
| Approx. | Approximately |
| Aq. | Aqueous |
| CHCl$_3$ | Chloroform |
| Cs$_2$CO$_3$ | Cesium carbonate |
| d | Day(s) |
| DCM | Dichloromethane |
| DDQ | 2,3-dichloro-5,6-dicyano-p-benzoquinone |
| DIAD | Diisopropylazodicarboxylate |
| DMAP | Dimethylaminopyridine |
| DME | 1,2-dimethoxyethane |
| DMF | N,N-dimethyl formamide |
| EtOAc | Ethyl acetate |
| h | Hour(s) |
| HATU | (dimethylamino)-N,N-dimethyl(3H-[1,2,3]triazolo[4,5-b]pyridin-3-yloxy)methaniminium hexafluorophosphate |
| HCl | hydrochloric acid |
| KOtBu | Potassium tert-butoxide |
| LC-MS | Liquid chromatography mass spectrum |
| min | Minute(s) |
| MeCN | Acetonitrile |
| MeOH | Methanol |
| MgSO$_4$ | Magnesium sulfate |
| MsCl | Methanesulfonyl chloride |
| N$_2$ | Nitrogen |
| NaBH$_4$ | Sodium borohydride |
| NaHCO$_3$ | Sodium bicarbonate |
| NaOH | Sodium hydroxide |
| Na$_2$SO$_4$ | Sodium sulfate |
| NMR | Nuclear magnetic resonance |
| Pd(OAc)$_2$ | Palladium acetate |
| PPh$_3$ | Triphenylphosphine |
| Prep | Preparative |
| pTSA | p-Toluenesulfonic acid |
| rt | Room temperature |
| SFC | Supercritical fluid chromatography |
| TEA | Triethylamine |
| THF | Tetrahydrofuran |
| TFA | Trifluoroacetic acid |
| TLC | Thin layer chromatography |

General:

All temperatures are in degrees Celsius (° C.) and are uncorrected.

Example 1: Synthesis of Trihexamidine Formate (Compound #1)

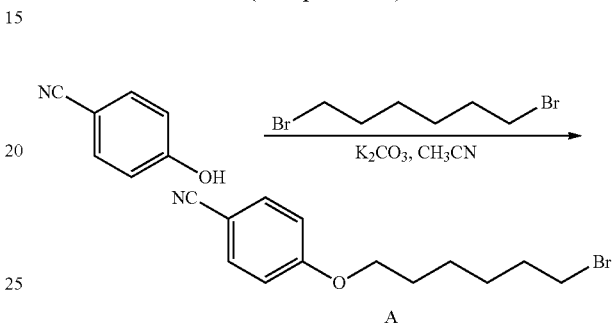

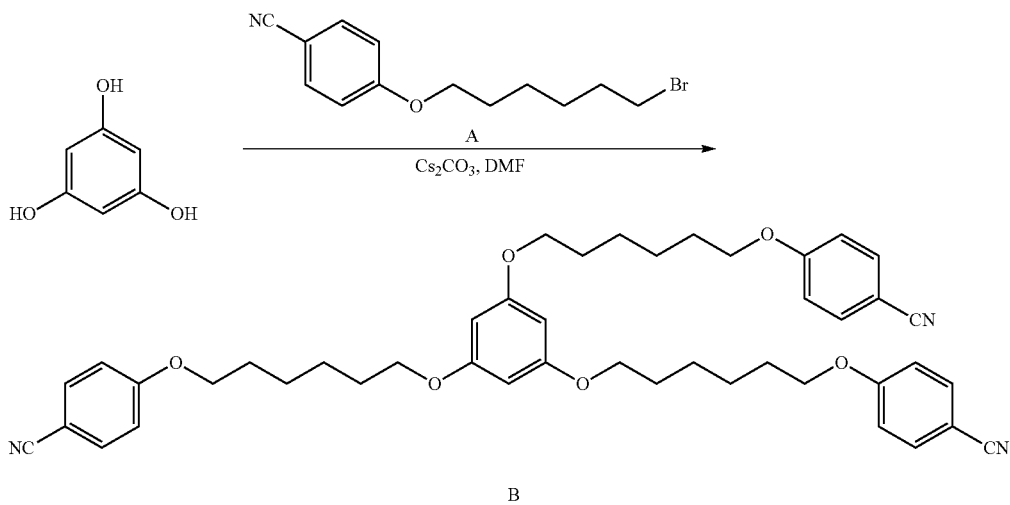

Step 1:

To 11.9 g (100 mM) of cyanophenol and potassium carbonate (20.7 g, 150 mM) was added CH$_3$CN (200 mL) and 1,6-dibromohexane (76 mL, 500 mM) and the mixture was refluxed over weekend. The mixture was cooled to room temperature, the solid was filtered off, washed with EtOAc, the solvent evaporated and the residue purified by combiflash to afford 23.95 g of A.

Step 2:

To the triphenol (1.05 g, 8.3 mM) was added DMF (30 mL), cesium carbonate (13.6 g, 41.6 mM) and the bromo A (11.7 g, 41.6 mM). The mixture was heated at 65° C. overnight. After cooling to room temperature the mixture was diluted with water, extracted with EtOAc (2×), washed with water (3×), brine, dried with Na$_2$SO$_4$, filtered and the solvent evaporated, after purification on the combiflash compound B (4.1 g) was obtained.

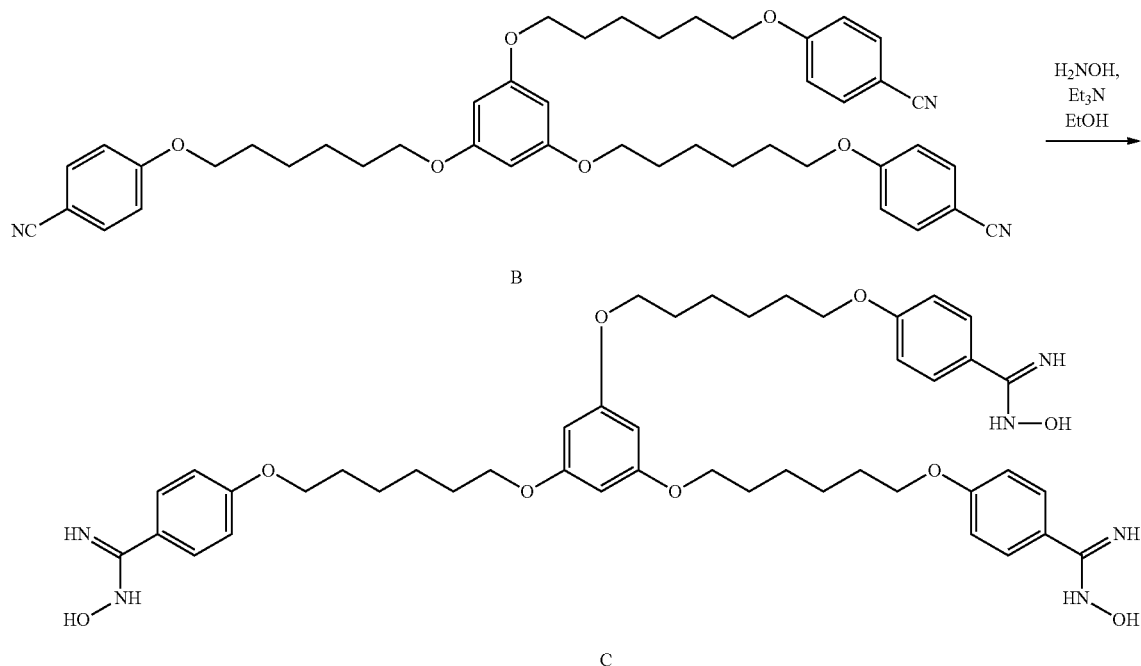
Step 3:
A mixture of tricyano B (271 mg, 0.37 mM), hydroxylamine hydrochloride (155 mg, 2.23 mM) and triethylamine (0.31 mL, 2.23 mM) in ethanol 15 mL was refluxed overnight. The solvent was evaporated, the residue purified on the combiflash to give 288 mg of C.
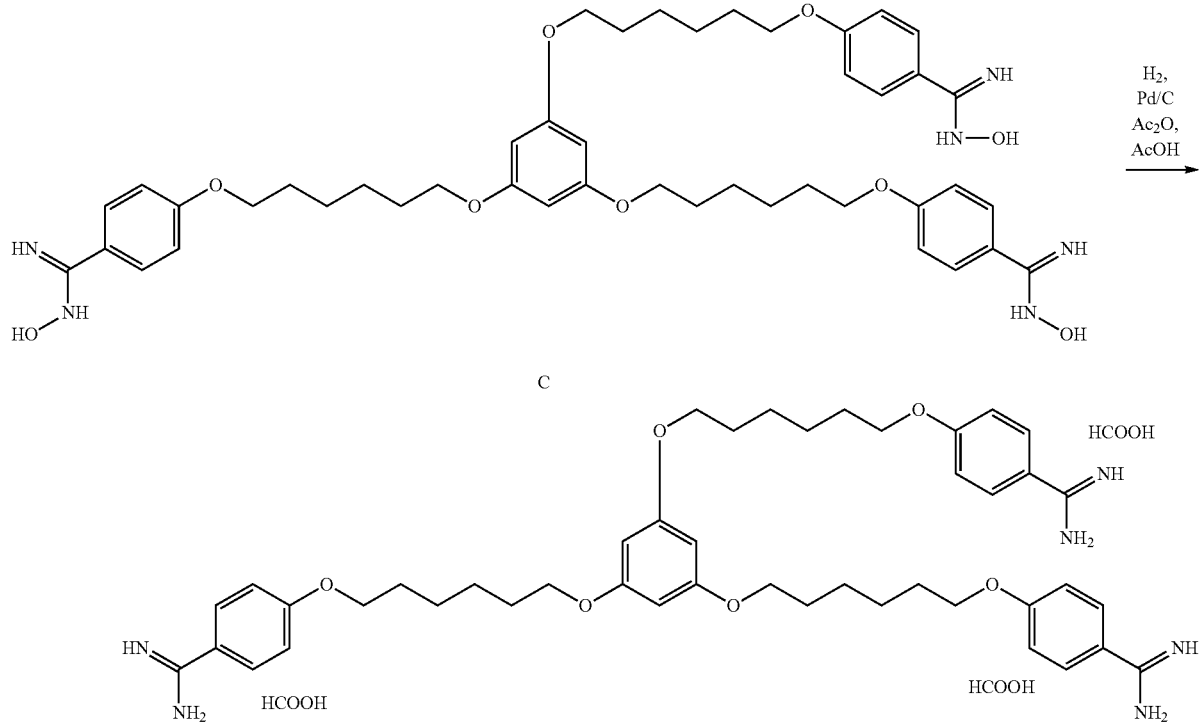
Ex. 1

Step 4:
C (288 mg, 0.34 mM) in AcOH (5 mL) was treated with Ac$_2$O (0.14 mL, 1.38 mM), the mixture stirred for 15 minutes then diluted with methanol (5 mL) and treated with Pd 10%/C (100 mg) under an atmosphere of H$_2$ (balloon) over night. Nitrogen was bubbled in the mixture which was then filtered on celite using methanol, the solvent was evaporated. The residue was purified using reverse phase prep HPLC C$_{18}$ column 25% CH$_3$CN/water (0.15 HCOOH), solvent evaporated, the residue lyophilized over night, giving 50 mg of the titled compound of Ex.1 as the formate salt.

Example 2: Synthesis of Trihexamidine Isethionate (Compound #2)

Compound #2 was prepared as generally presented in Example 1. Synthesis was modified to provide the proper ratio of isethionate salt, as presented below:

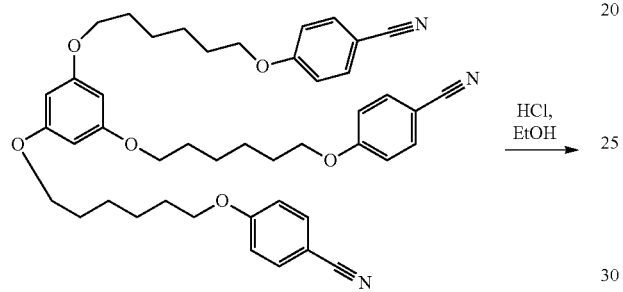

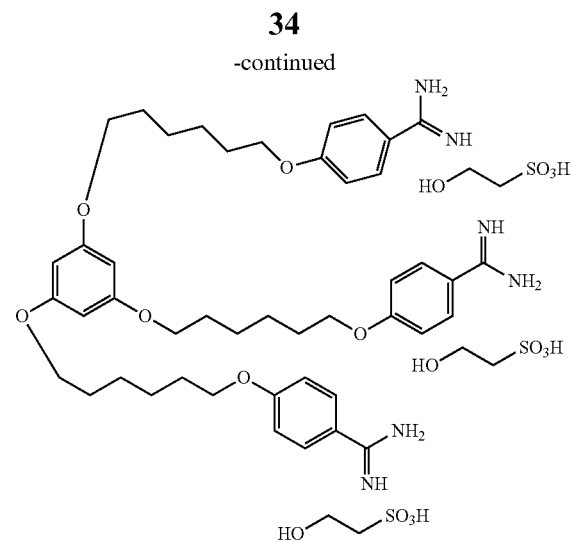

Example 3: Synthesis of Trioctamidine Isethionate (Compound #3)

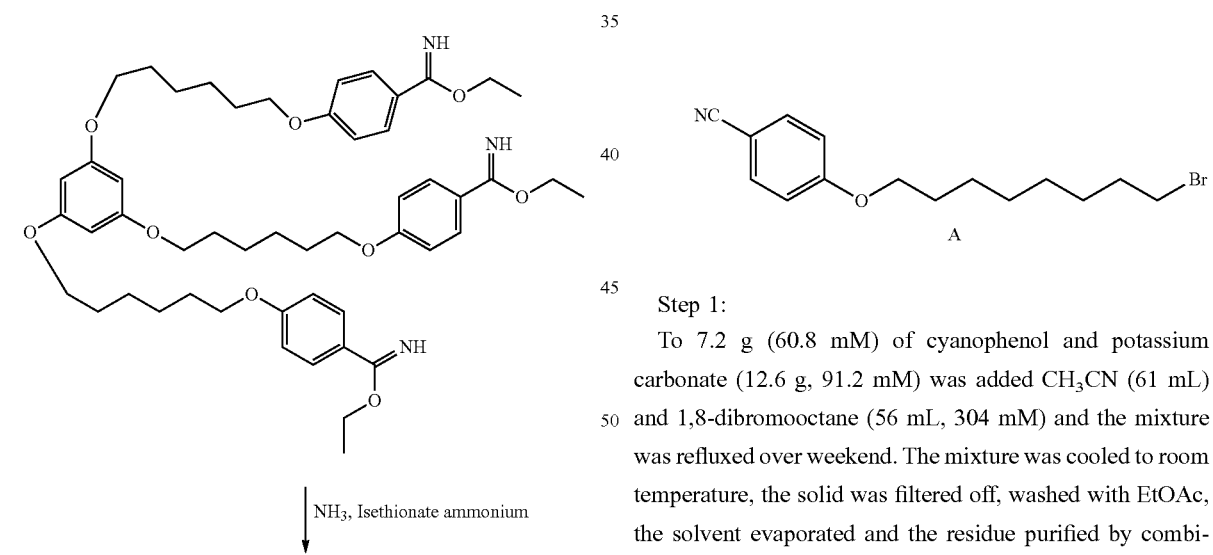

Step 1:

To 7.2 g (60.8 mM) of cyanophenol and potassium carbonate (12.6 g, 91.2 mM) was added CH$_3$CN (61 mL) and 1,8-dibromooctane (56 mL, 304 mM) and the mixture was refluxed over weekend. The mixture was cooled to room temperature, the solid was filtered off, washed with EtOAc, the solvent evaporated and the residue purified by combi-flash to afford 15 g of A.

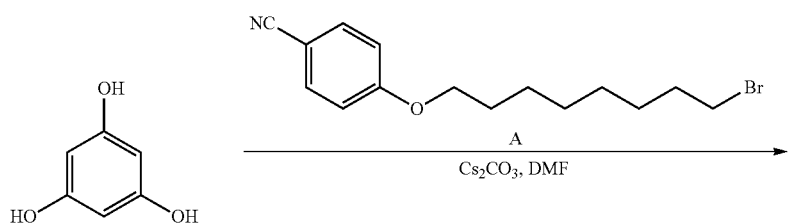

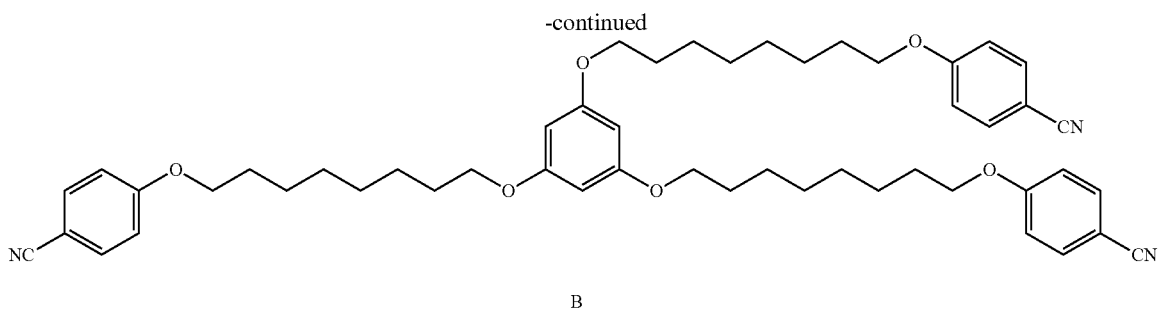

B

Step 2:
To the triphenol (894 mg, 7.1 mM) was added DMF (30 mL), cesium carbonate (11.5 g, 35.4 mM) and the bromo A (11 g, 35.4 mM). The mixture was heated at 65° C. over night. After cooling to room temperature the mixture was diluted with water, extracted with EtOAc (2×), washed with water (4×), brine, dried with $Na_2SO_4$, filtered and the solvent evaporated, after purification on the combiflash compound B (1.32 g pure and 2.8 g impure) was obtained.

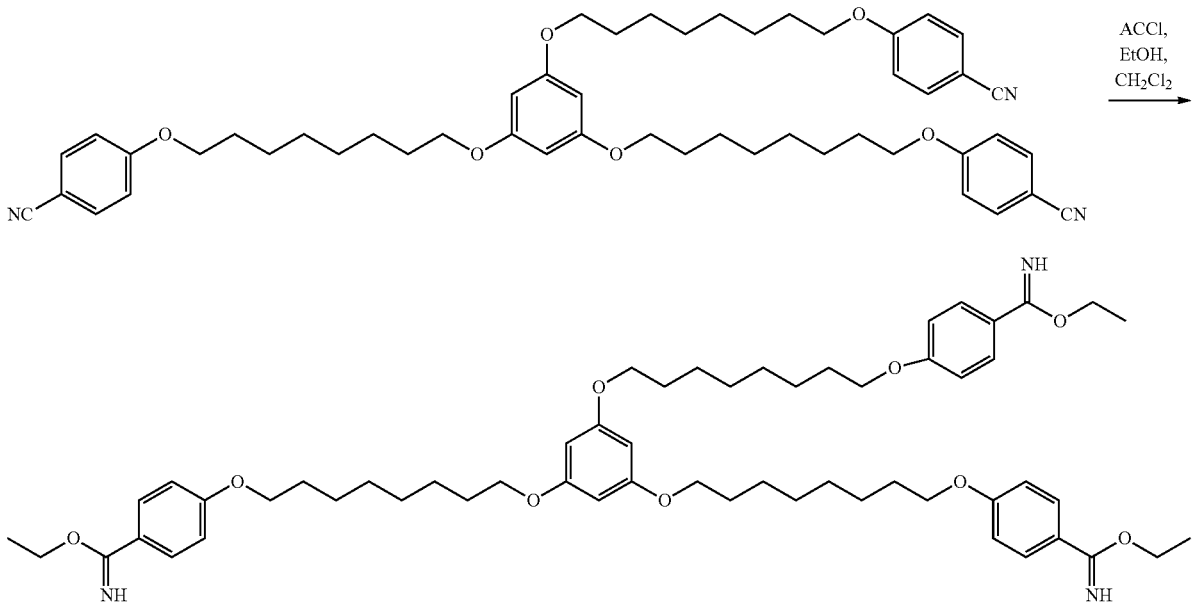

Step 3:
To tricyano (1 g, 1.23 mM), in ethanol (6 mL) and dichloromethane (8 mL) in an ice water bath was added acetyl chloride (4.6 mL) the mixture was stoppered and stirred over weekend at room temperature. The mixture was diluted with $CH_2Cl_2$, washed with saturated $NaHCO_3$ (2×), brine, dried over $Na_2SO_4$, filtered evaporated and purified on the combiflash, giving 962 mg of product.

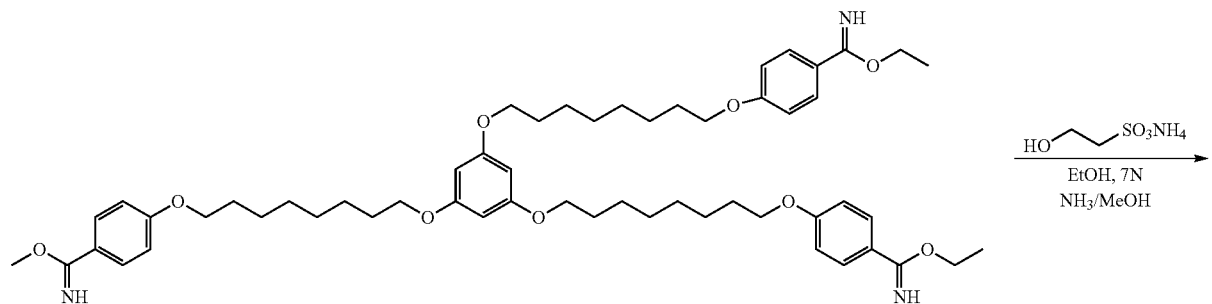

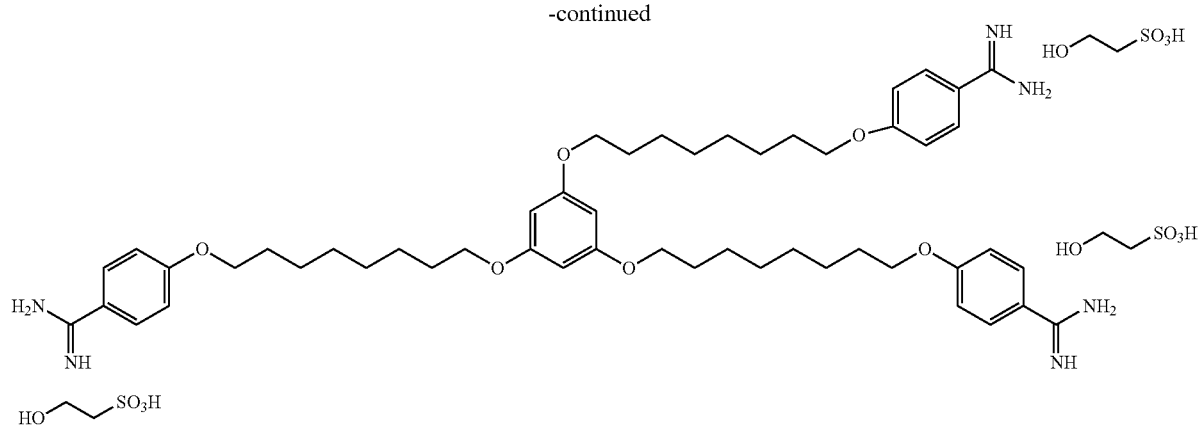

Step 4:

To 93.5 mg (0.09 mM) of starting material in ethanol (2 mL) and 7N NH$_3$ in methanol (4 mL) was added ammonium isethionate (38.7 mg, 0.27 mM) and the mixture was heated at 65 C, cooled to room temperature, the solvent was evaporated and coevaporated with water (2×), the residue was freeze dried over night giving 96 mg of the titled compound of Example 3.

Example 4: Synthesis of Tripropamidine Formate (Compound #4)

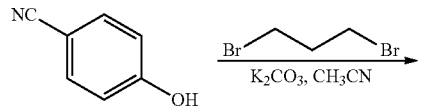

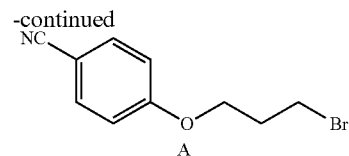

Step 1:

To 11.9 g (100 mM) of cyanophenol and potassium carbonate (20.7 g, 150 mM) was added CH$_3$CN (200 mL) and 1,3-dibromopropane (50.7 mL, 500 mM) and the mixture was refluxed overnight. The mixture was cooled to room temperature, the solid was filtered off, the solvent evaporated, diluted with ether, filtered again, the solvent evaporated and the residue purified by combiflash to afford A.

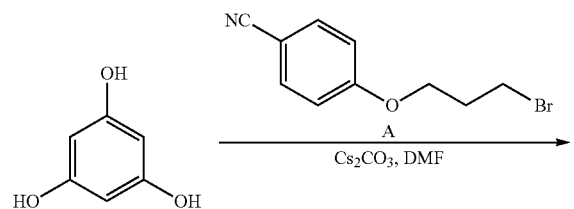

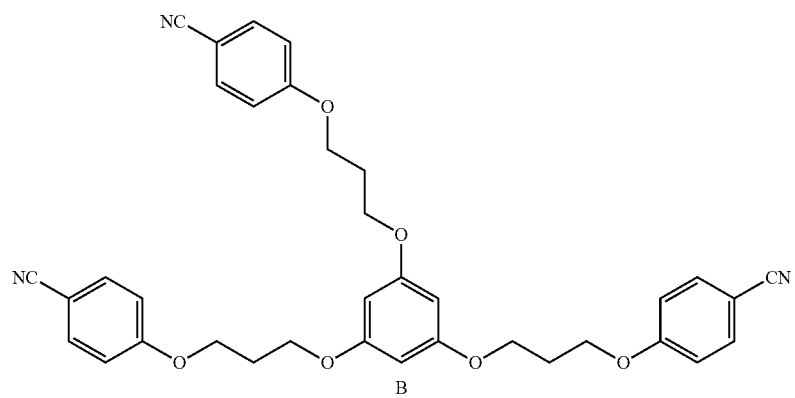

Step 2:

To the triphenol (1.05 g, 8.3 mM) was added DMF (30 mL), cesium carbonate (13.6 g, 41.6 mM) and the bromo A (10 g, 41.6 mM). The mixture was heated at 65° C. over night. After cooling to room temperature the mixture was diluted with water, extracted with EtOAc (2×), washed with water (3×), brine, dried with $Na_2SO_4$, filtered and the solvent evaporated, after purification on the combiflash compound B was obtained.

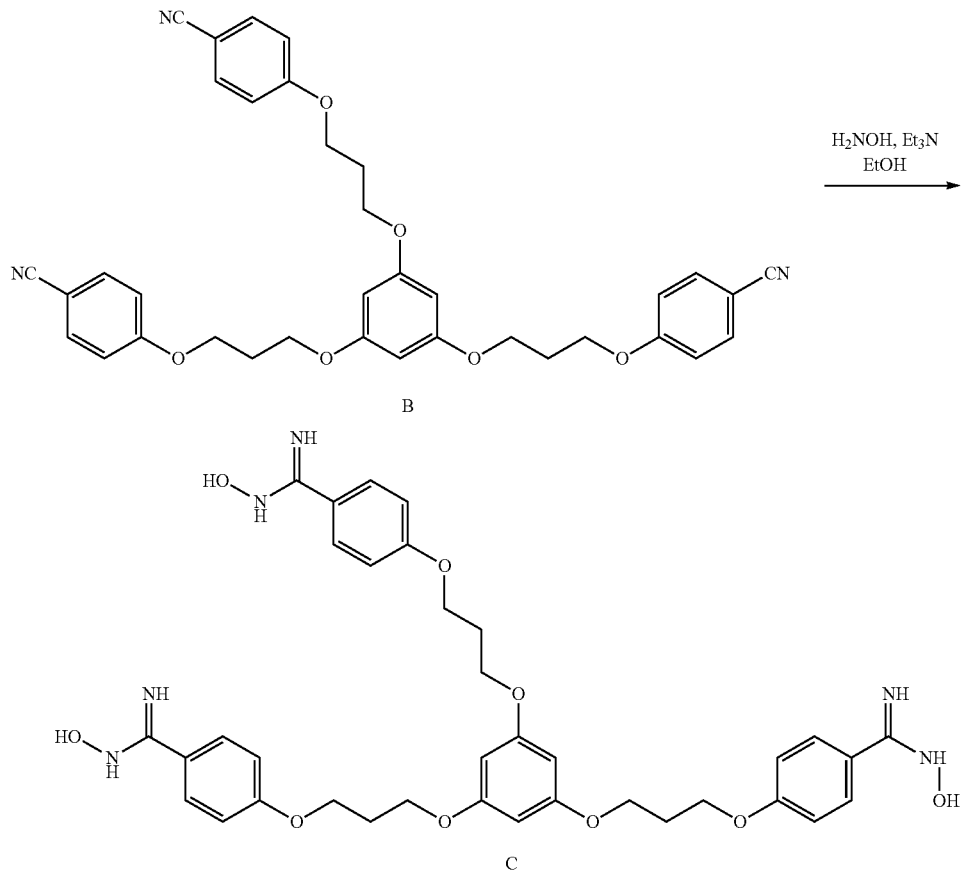

Step 3:

A mixture of tricyano B (430 mg, 0.71 mM), hydroxylamine hydrochloride (297 mg, 4.27 mM) and triethylamine (0.59 mL, 4.27 mM) in ethanol 20 mL was refluxed over night. Upon cooling the product solidified and was filtered, washed with ethanol, air dried, giving 340 mg of C.

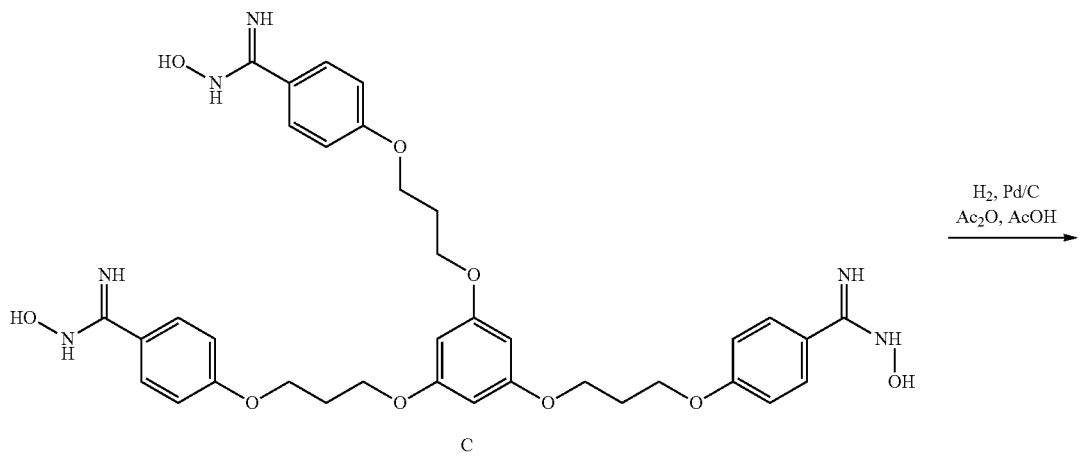

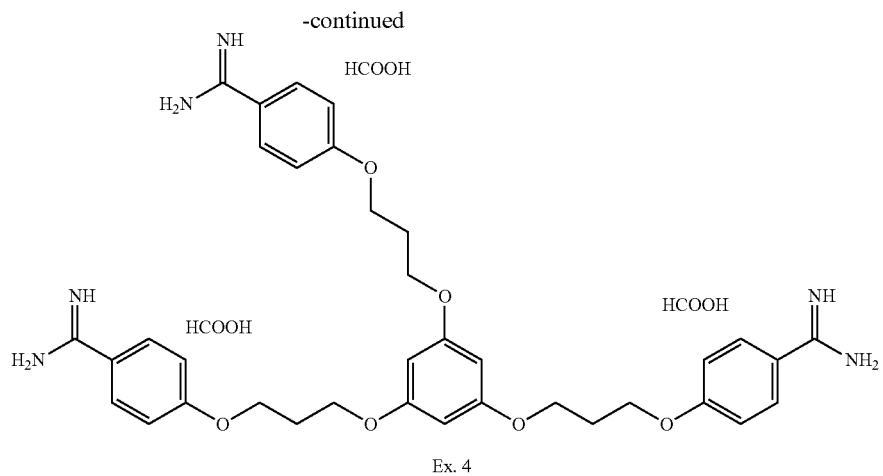

Ex. 4

Step 4:

C (340 mg, 0.48 mM) in AcOH (7 mL) was treated with Ac₂O (0.21 mL, 2.18 mM), the mixture stirred for 15 minutes then diluted with methanol (5 mL) and treated with Pd 10%/C (100 mg) under an atmosphere of H$_2$ (balloon) over night. Nitrogen was bubbled in the mixture which was then filtered on celite using methanol, the solvent was evaporated. The residue was purified using reverse phase prep HPLC C$_{18}$ column 25% CH$_3$CN/water (0.15 HCOOH), solvent evaporated, the residue lyophilized over night, giving 122 mg of the titled compound of Ex.4 as the formate salt.

Example 5: Synthesis of Triamidine Formate (Chain Average Mn 1000) (Compound #5)

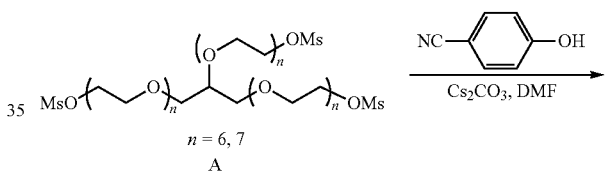

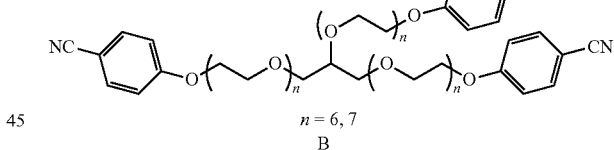

Step 1:

To a solution of glycerol ethoxylate (10 g, 10 mM) in CH$_2$Cl$_2$ (50 mL), THF (50 mL) and triethylamine (5.4 mL, 39 mM) in an ice/water bath was slowly added methanesulfonyl chloride (2.6 mL, 33 mM), the mixture was stirred over night at room temperature. The mixture was diluted with water, organics separated, the water reextracted with CH$_2$Cl$_2$, organics combined, dried with Na$_2$SO$_4$, filtered and the solvent evaporated. Giving 14.32 g of A.

Step 2:

The crude from A (10 mM) was dissolved in DMF (50 mL), cesium carbonate (19.5 g, 60 mM) and 4-cyanophenol (5.96 g, 50 mM) were added and the mixture was heated over night at 60° C. After cooling to room temperature the mixture was diluted with water, extracted with EtOAc (2×), washed with water (3×), brine, dried with Na$_2$SO$_4$, filtered and the solvent evaporated. Purification on the combiflash afforded 11.2 g of B.

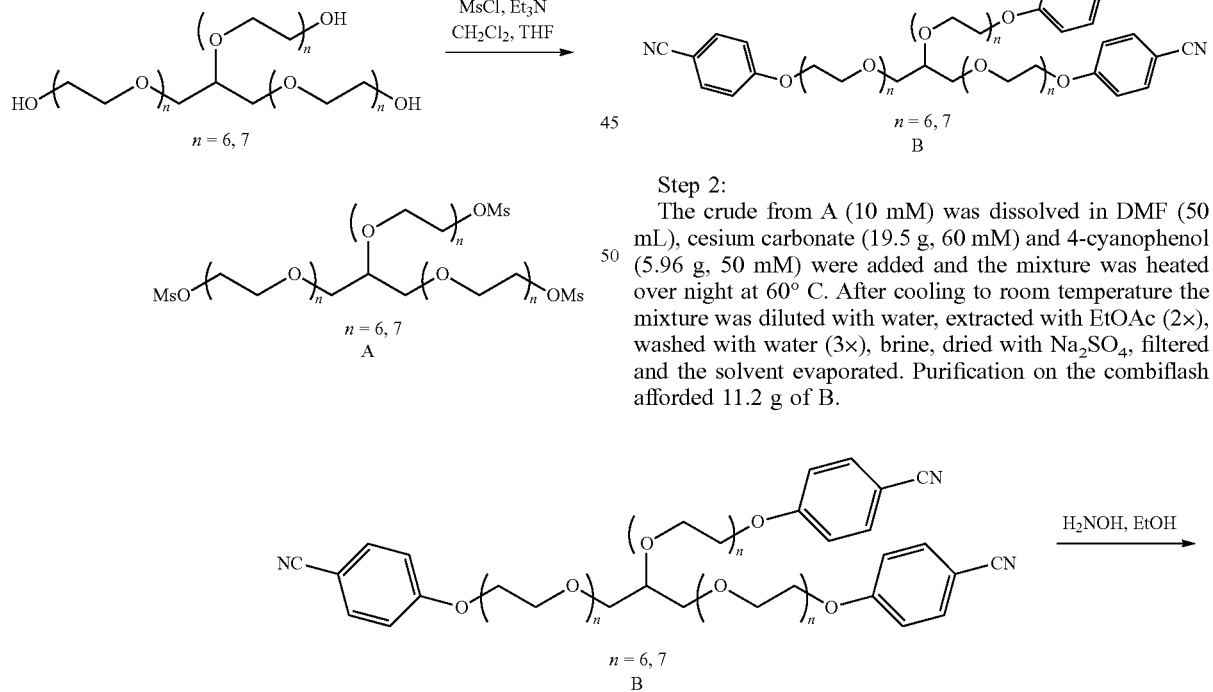

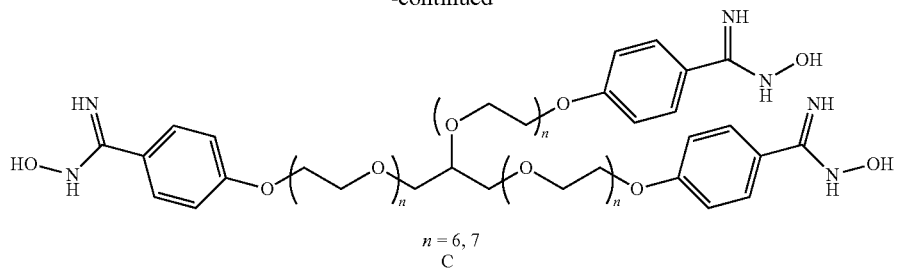

n = 6, 7
C

Step 3:

A solution of B (4.4 g, 3.4 mM), hydroxylamine hydrochloride (1.42 g, 20.4 mM), triethylamine (2.84 mL, 20.4 mM) in ethanol (150 mL) was refluxed over night, the solvent was then evaporated and the residue purified by combiflash 0% to 50% methanol/$CH_2Cl_2$, giving 2.63 g of C.

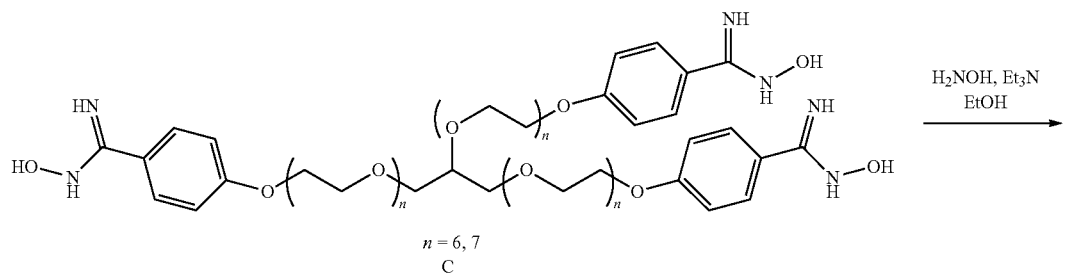

n = 6, 7
C

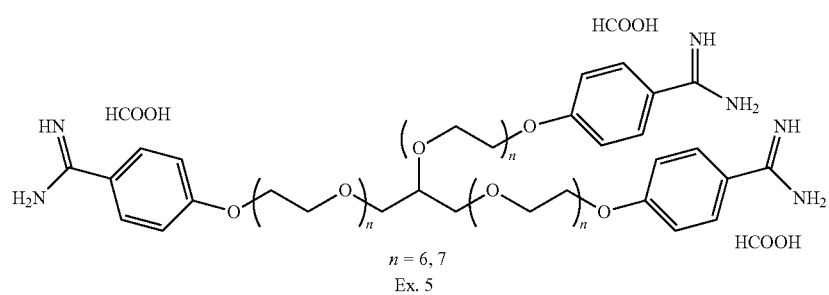

n = 6, 7
Ex. 5

Step 4:

C (1 g, 0.71 mM) in AcOH (10 mL) was treated with $Ac_2O$ (0.33 mL, 3.46 mM), the mixture stirred for 15 minutes then diluted with methanol (5 mL) and treated with Pd 10%/C (100 mg) under an atmosphere of $H_2$ (balloon) over night. Nitrogen was bubbled in the mixture which was then filtered on celite using methanol, the solvent was evaporated. The residue was purified using a silica gel column on the combiflash 0% to 80% methanol/$CH_2Cl_2$, methanol containing 5% HCOOH, giving 65 mg of the titled compound of Ex.5. Low resolution Mass Spectroscopy (+): 1371.9 [M+1].

Example 6: HCT Assay

The compounds were evaluated in a proliferation assay using HCT-116 cells using an xCELLigence system. The results are shown in Table 2 below. Briefly, the xCELLigence system monitors cellular events in real time by measuring electrical impedance across interdigitated microelectrodes integrated on the bottom of tissue culture E-Plates. The impedance measurement provides quantitative information about the biological status of the cells, including cell number, viability, and morphology. Real-time proliferation assays were then to determine the IC50 values. All proliferation assays start 24 hours after the transfection.

TABLE 2
| Compound | Structure | Mw | HCT-116 IC50 (μM) |
|---|---|---|---|
| 1 | 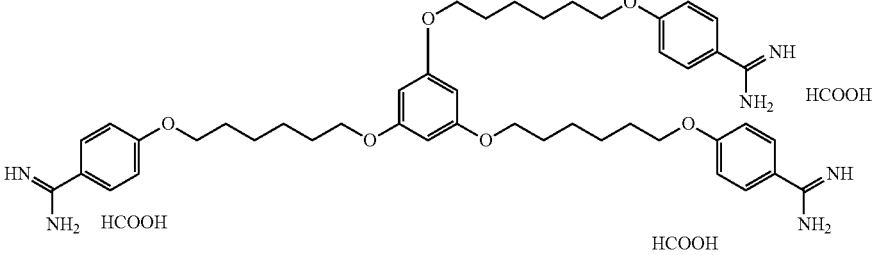 | Parent: 780.99 Salt: 919.07 g/mol | 1.9 |
| 2 | 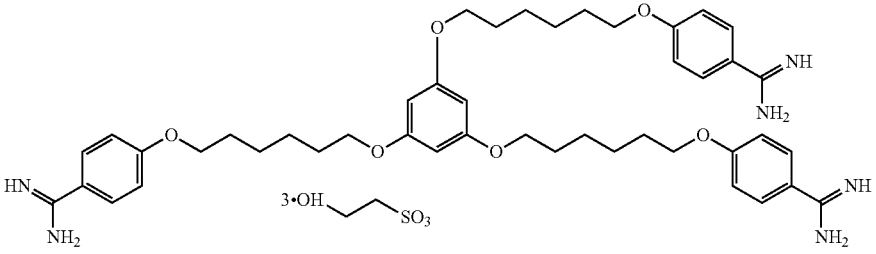 | Parent: 780.99 Salt: 1159.39 g/mol | 2.66 |
| 3 | 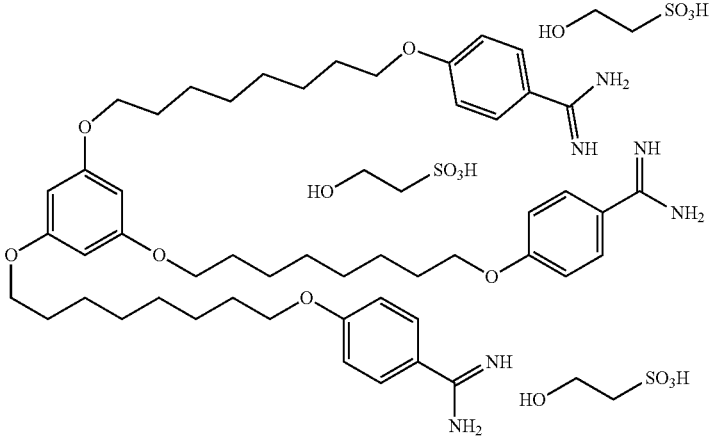 | Parent: 865.1 g/mol Salt: 1243.55 g/mol | 6.67 |
| 4 | 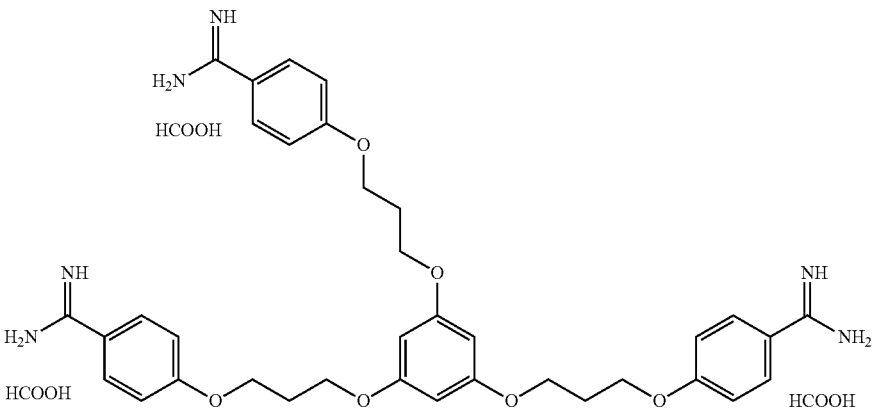 [SMILES: "HCOOH" ; N=C(N)c1ccc(OCCCOc2cc(OCCCOc3ccc(C(=N)N)cc3)cc(OCCCOc3ccc(C(=N)N)cc3)c2)cc1 ; "HCOOH" ; "HCOOH"] | Parent: 654.76 Salt: 792.83 g/mol | 38 |

TABLE 2-continued

| Compound | Structure | Mw | HCT-116 IC50 (µM) |
|---|---|---|---|
| 5 | 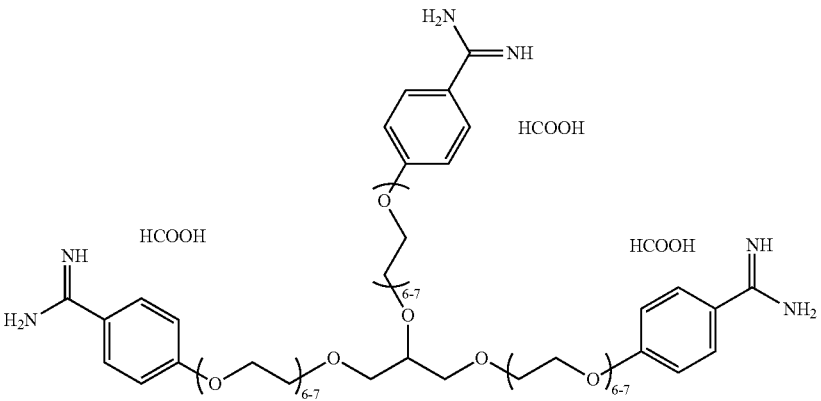 | (weight average molecular weight) Parent: 1371.61 by MS main peak Salt: 1509.68 g/mol | ∞ |

Example 7: GalN/LPS Fulminant Liver Injury Model: An Anti-Inflammatory, Anti-TNFα, Hepatoprotection Model A Galactosamine/Liposaccharide (GalN/LPS) fulminant liver injury model may be used to evaluate the anti-inflammatory, anti-TNFα and hepatoprotective properties of the compound of the description.

Mice were maintained under 12 h light/dark cycles with unlimited access to food and water. Study was performed in 6- to 14-week old male mice. C57BL/6 mice were used. Mice are first injected with pentamidine or Example 2 compound (IP injection). 30 minutes later, liver injury is induced by intraperitoneal injections of 100 µg/kg of LPS (*E. coli* 0111:B4) and 700 mg/kg of GalN (Sigma) dissolved in phosphate-buffered saline (PBS).

Study a

The tested compounds were be dosed IP 30-minutes prior to the co-treatment with galactosamine (GalN) and endotoxin (Lipopolysaccharide) LPS. Mice were either sacrificed at 6.5 hours after GalN/LPS for ALT analysis, or kept for longer periods to evaluate survival. The analysis of alanine transaminase (ALT) serum levels and histological observations allow the evaluation of the hepatoprotective, anti-TNF-α, anti-inflammatory and/or anti-fibrotic activity.

Survival was evaluated at two time points, i.e. 8 and 23 hours. In controls group receiving PBS prior to the GalN/LPS liver injury, no mice survived 8 hours. In groups treated with control pentamidine at doses of 25 and 40 mg/kg, only the 40 mg/kg (67 µmole/kg) group benefited from hepatoprotective properties of pentamidine at 8 hours, but none survived 23 hours. In the case of trihexamidine isethionate, all mice survived more than 23 hours with 10 mg/kg (8.6 µmole/kg) doses. These results strongly support the hepatoprotective activity of triamidines (FIGS. 1 and 2).

Study b

All doses were administered IP to six mice (n=6), 30 minutes prior to the injection of the GalN and LPS, when applicable to the group. Blood samples were collected exactly 6 hours post GalN/LPS injections, or 6.5 hours after vehicle injections.

| Tx (IP) | IP Dose (mg/kg in WFI) | GalN - LPS doses | ALT (IU/L) |
|---|---|---|---|
| Sterile WFI | N/A | 700 mg/kg - 10 µg/kg | 5989 |
| Pentamidine | 50 | 700 mg/kg - 10 µg/kg | 306 |
| Compound 4 (C4) | 5 | 700 mg/kg - 10 µg/kg | 731 |
| Compound 5 (C5) | 5 | 700 mg/kg - 10 µg/kg | 1072 |
| Compound 5 (C5) | 10 | 700 mg/kg - 10 µg/kg | 689 |
| Compound 2 (C2) | 5 | 700 mg/kg - 10 µg/kg | 2184 |
| Compound 2 (C2) | 10 | 700 mg/kg - 10 µg/kg | 890 |

The tested compounds were dosed IP 30 minutes prior to the co-treatment with galactosamine (GalN) and endotoxin (Lipopolysaccharide) LPS. Mice were sacrificed at 6 hours after GalN/LPS for ALT analysis. The analysis of alanine transaminase (ALT) serum levels allows the evaluation of the hepatoprotective, anti-TNF-α, anti-inflammatory and/or anti-fibrotic activity.

Results indicate that Compounds 2, 4 and 5 (C2, C4, C5) are hepatoprotective in the model, as shown by low ALT activity levels following the injection of GalN/LPS. See FIG. 3. Animals treated with pentamidine at the dose of 50 mg/kg (84 µmole/kg) benefited from hepatoprotective properties of pentamidine (positive control, Penta-50 mpk). Significant hepatoprotection was also provided by lower doses: 10 mg/kg (4.3 and 8.6 µmole/kg) for C2, 5 and 10 mg/kg (3.3 and 6.6 µmole/kg) for C4 and 5 mg/kg (6.3 mole/kg) for C5. These results strongly support the hepatoprotective activity of the tested compounds (FIG. 3).

Study c

All doses were administered IP to six mice (n=6), 30 minutes prior to the injection of the GalN and LPS, when applicable to the group. Blood samples were collected exactly 6 hours post GalN/LPS injections, or 6.5 hours after vehicle injections.

| Tx (IP) | IP Dose (mg/kg in WFI) | GalN - LPS doses | ALT (IU/L) |
|---|---|---|---|
| Sterile WFI | N/A | 700 mg/kg - 10 µg/kg | 4403 |
| Compound 4 (C4) | 0.625 | 700 mg/kg - 10 µg/kg | 1755 |
| Compound 4 (C4) | 1.25 | 700 mg/kg - 10 µg/kg | 1090 |
| Compound 4 (C4) | 2.5 | 700 mg/kg - 10 µg/kg | 555 |

The tested compounds were dosed IP 30 minutes prior to the co-treatment with galactosamine (GalN) and endotoxin (Lipopolysaccharide) LPS. Mice were sacrificed at 6 hours after GalN/LPS for ALT analysis. The analysis of alanine transaminase (ALT) serum levels allows the evaluation of the hepatoprotective, anti-TNF-α, anti-inflammatory and/or anti-fibrotic activity.

Results indicate that Compound 4 (C4) provides a dose-dependent hepatoprotection in the model, as shown by low ALT activity levels following the injection of GalN/LPS. See FIG. 4. Animals treated with pentamidine at the dose of 50 mg/kg (84 µmole/kg) benefited from hepatoprotective properties of pentamidine (positive control, Penta-50 mpk). Significant hepatoprotection was also provided by C4 at 0.625 mg/kg (0.8 mole/kg), 1.25 mg/kg (1.6 mole/kg) and 2.5 mg/kg (3.2 mole/kg) for C5. These results strongly support the hepatoprotective activity of the tested compounds (FIG. 4).

Example 8

DSS-Induced Acute Colitis in Mice (Compound 2 and Compound 4)
Study Summary
Formulation Dextran Sulfate Sodium 2.5% stocks were prepared by adding tap water in the pre-weighed powder. DSS solutions will be changed every 3 days for all groups, i.e. on Day 1 (D1) and Day 4 (D4).

Formulations for Intraperitoneal Administration:
Vehicle: sterile double distilled water (DDW)
For Pentamidine (Penta) and Compounds 2 and 4, the compounds were dissolved in DDW and dosed at 2 mL/kg to yield the indicated doses.

In-Vivo Study

Male C57BL/6 ELITE mice of ~7-8 weeks old were used. After 5-day acclimatization period in animal facility, all mice were weighed and given tap water containing 2.5% DSS on Day 1, treatment also starts on Day 1.

Husbandry

The animal room environment is controlled (temperature 22±0.2° C.; relative humidity 55±25%; 12 hours light/dark cycle, and 12 air changes per hour). A standard certified commercial rodent chow is provided to the animals ad libitum. Procedures involving the care and use of animals in this study will be reviewed and approved by the Institutional Animal Care and Use Committee (IACUC) prior to conduct.

Treatment and Daily Observations

On the morning of Day 1 (D1), the drinking water will be replaced by 2.5% DSS-containing tap water.

Animals were dosed from D1 to D6, once daily by IP injection (2 mL/kg). Animals were terminated on D7. The Disease Activity Index (DAI) scale is based on the evaluation of different parameters characterizing experimental colitis induction and progression. Body weight, presence of gross blood in the feces and stool consistency will be recorded daily.

Disease Accumulated Index is Determined by Scoring Changes in:
Weight loss: 0=none; 1=1 to 5%; 2=5 to 10%; 3=_10 to 20%; 4=>20%
Stool consistency: 0=normal; 2=loose; 4=diarrhea
Rectal bleeding: 0=normal; 2=occult bleeding; 4=gross bleeding Moreover, animals will be monitored for pain level and hydration. If they seem in distress or obtain a final Disease Activity Index of 12 points (per mouse), they will be considered reaching clinical end point for euthanasia.

Termination

On Day 7, mice will be weighed and disease scores evaluated, and then euthanized by $CO_2$ inhalation.

CONCLUSION

Compounds 2 and 4 have reduced the disease activity index in the DSS-induce acute colitis model, demonstrating their potential in treating GI disorders related to inflammatory conditions. The results are shown in FIG. 5.

The invention claimed is:
1. A compound of formula (I):

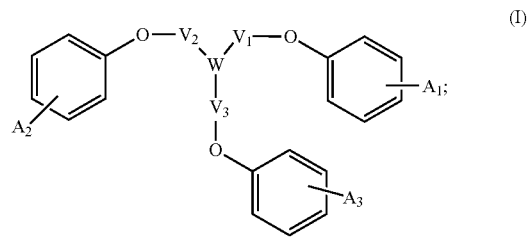

or a pharmaceutically acceptable salt thereof,

TABLE 1

| Groups | | | | | | | | |
|---|---|---|---|---|---|---|---|---|
| Group | compound | DSS dose | Dose (mg/kg) | volume | route | frequency | duration | termination |
| 1 | DDW | 2.5% | — | 2 mL/kg | IP | q.d. | D1-D6 | D7 |
| 2 | Pentamidine | 2.5% | 5 | 2 mL/kg | IP | q.d. | D1-D6 | D7 |
| 3 | Compound 2 | 2.5% | 2.5 | 2 mL/kg | IP | q.d. | D1-D6 | D7 |
| 4 | Compound 2 | 2.5% | 5 | 2 mL/kg | IP | q.d. | D1-D6 | D7 |
| 5 | Compound 4 | 2.5% | 2.5 | 2 mL/kg | IP | q.d. | D1-D6 | D7 |
| 6 | Compound 4 | 2.5% | 5 | 2 mL/kg | IP | q.d. | D1-D6 | D7 | wherein:

W is a carbon atom or phenyl;

$V_1$, $V_2$ and $V_3$ are each independently $C_3$-$C_{12}$ alkyl, $C_3$-$C_{12}$ alkyl interrupted by —O—, —$OC_3$-$C_{12}$ alkyl or —$OC_3$-$C_{12}$ alkyl wherein the $C_3$-$C_{12}$ alkyl is interrupted by —O—; and $A_1$, $A_2$ and $A_3$ are each independently —C(=NH)—$NH_2$ or —C(=NH)—NHOH;

provided that when $V_1$, $V_2$ and $V_3$ are —$(CH_2)_{1-6}$-; then at least one of $A_1$, $A_2$ and $A_3$ is C(=NH)—NHOH.

2. The compound according to claim 1, wherein W is phenyl.

3. The compound according to claim 1, wherein W is a carbon atom.

4. The compound according to claim 1, wherein $V_1$, $V_2$ and $V_3$ are each independently $C_3$-$C_{12}$ alkyl or $C_3$-$C_{12}$ alkyl interrupted by —O—.

5. The compound according to claim 1, wherein $V_1$, $V_2$ and $V_3$ are each independently $C_5$-$C_{12}$ alkyl or $C_5$-$C_{12}$ alkyl interrupted by —O—.

6. The compound according to claim 1, wherein $V_1$, $V_2$ and $V_3$ are each $C_3$-$C_{12}$ alkyl.

7. The compound according to claim 1, wherein $V_1$, $V_2$ and $V_3$ are each $C_5$-$C_{12}$ alkyl.

8. The compound according to claim 1, wherein $V_1$, $V_2$ and $V_3$ are each independently —$OC_3$-$C_{12}$ alkyl or —$OC_3$-$C_{12}$ alkyl interrupted by —O—.

9. The compound according to claim 1, wherein $V_1$, $V_2$ and $V_3$ are each independently —$OC_5$-$C_{12}$ alkyl or —$OC_5$-$C_{12}$ alkyl interrupted by —O—.

10. The compound according to claim 1, wherein $V_1$, $V_2$ and $V_3$ are each —$OC_3$-$C_{12}$ alkyl.

11. The compound according to claim 1, wherein $V_1$, $V_2$ and $V_3$ are each —$OC_5$-$C_{12}$ alkyl.

12. The compound according to claim 1, wherein the compound of formula (I) is represented by:

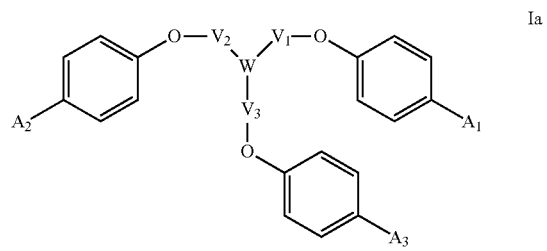

wherein W, $V_1$, $V_2$, $V_3$, $A_1$, $A_2$ and $A_3$ are as defined in claim 1.

13. The compound according to claim 1, where the compound is:

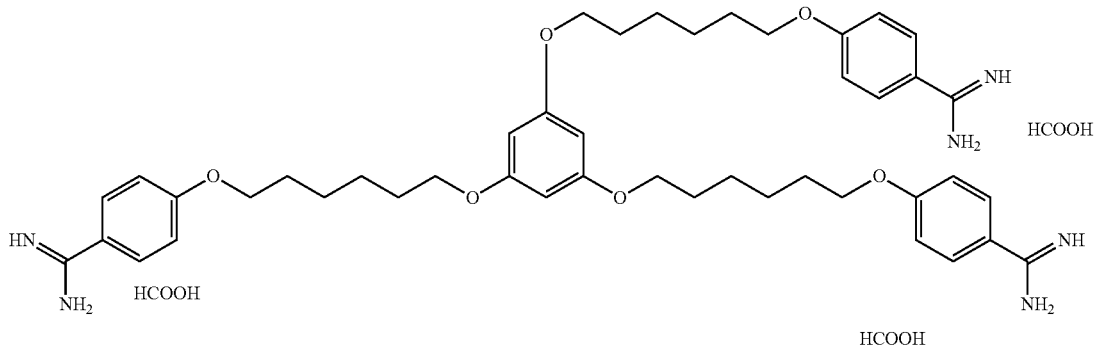

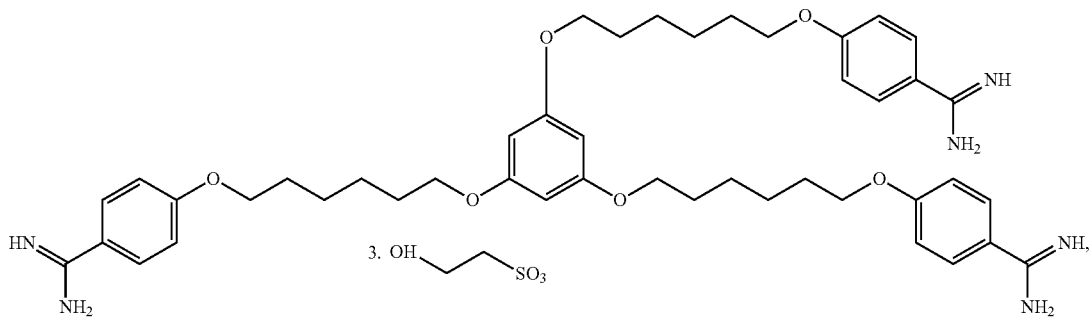

-continued
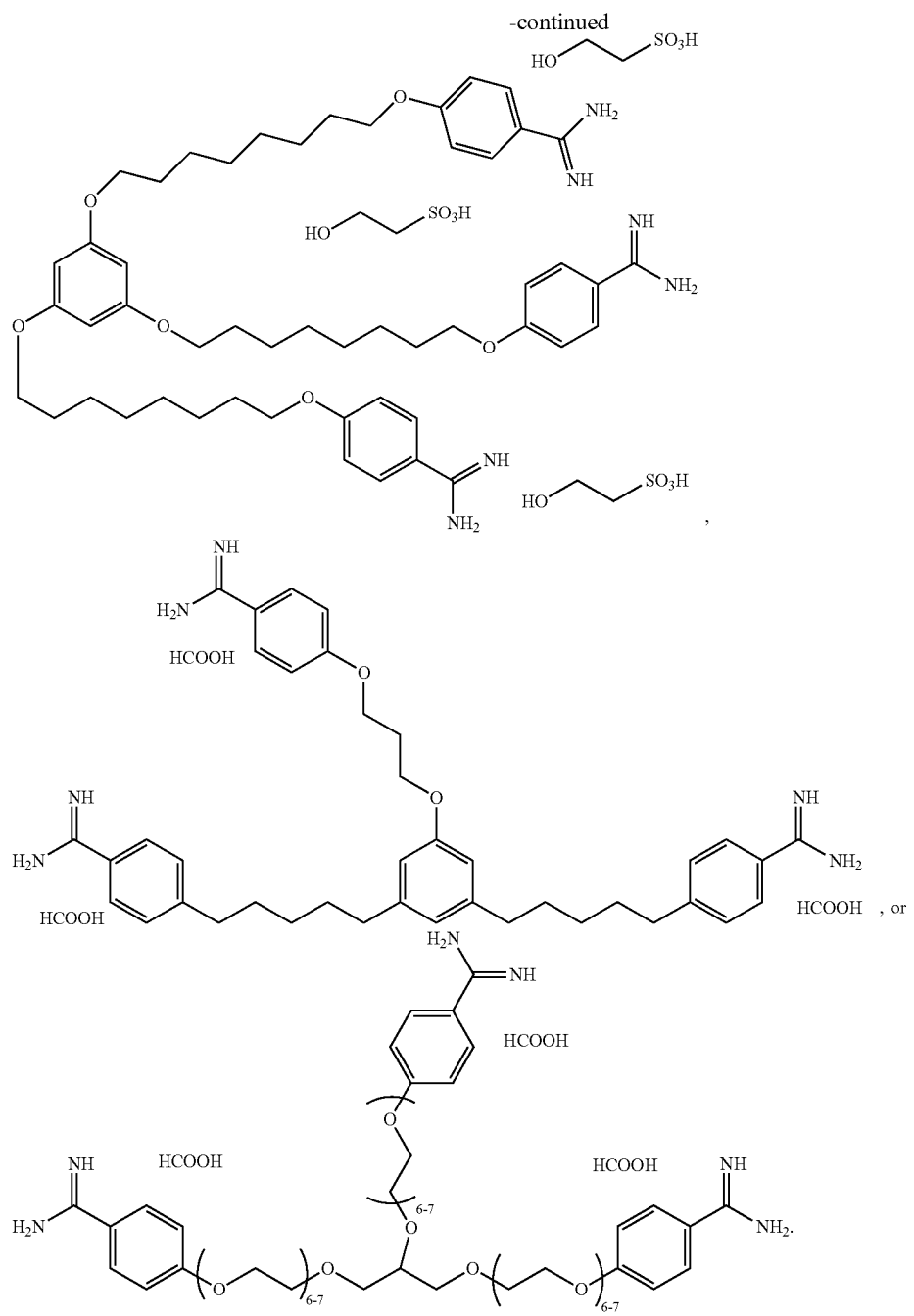
14. A pharmaceutical composition comprising a compound according to claim 1 with a pharmaceutically acceptable carrier, diluent and excipient.
* * * * *

UNITED STATES PATENT AND TRADEMARK OFFICE
CERTIFICATE OF CORRECTION

PATENT NO. : 11,098,009 B2
APPLICATION NO. : 16/470922
DATED : August 24, 2021
INVENTOR(S) : François Ravenelle et al.

Page 1 of 1

It is certified that error appears in the above-identified patent and that said Letters Patent is hereby corrected as shown below:

In the Claims

In Column 53, Claim 13, delete the compound:

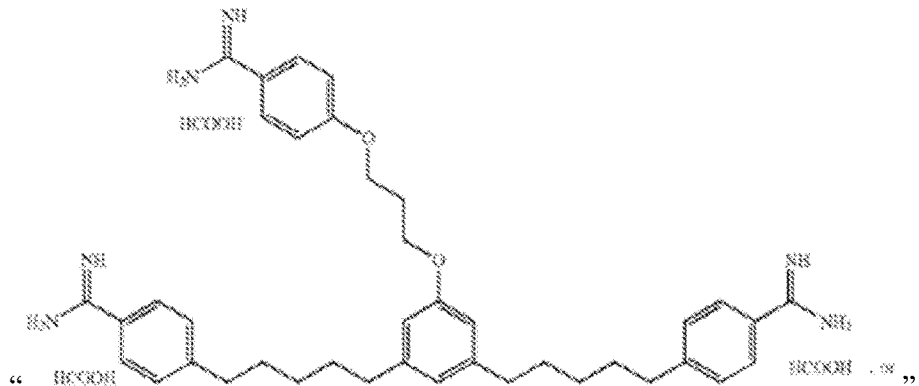

And replace with:

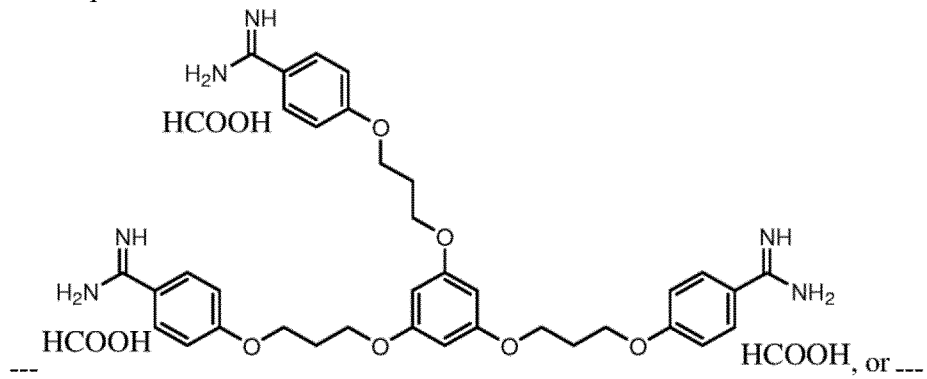

Signed and Sealed this
Twenty-eighth Day of December, 2021

Drew Hirshfeld
*Performing the Functions and Duties of the
Under Secretary of Commerce for Intellectual Property and
Director of the United States Patent and Trademark Office*